(12) United States Patent
La Voie et al.

(10) Patent No.: US 6,486,167 B1
(45) Date of Patent: *Nov. 26, 2002

(54) HETEROCYCLIC CYTOTOXIC AGENTS

(75) Inventors: Edmond J. La Voie, Princeton Junction; Darshan B. Makhey, Edison; Baoping Zhao, Highland Park; Leroy Fong Liu, Bridgewater, all of NJ (US)

(73) Assignee: Rutgers, The State University of New Jersey, Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/581,365
(22) PCT Filed: Dec. 11, 1998
(86) PCT No.: PCT/US98/26292
§ 371 (c)(1),
(2), (4) Date: Sep. 29, 2000
(87) PCT Pub. No.: WO99/31067
PCT Pub. Date: Jun. 24, 1999

Related U.S. Application Data

(63) Continuation of application No. 08/989,576, filed on Dec. 12, 1997, now Pat. No. 6,140,328.

(51) Int. Cl.[7] .............................................. A01N 43/42
(52) U.S. Cl. ........................ 514/284; 514/285; 514/280; 514/248; 544/233; 546/48; 546/61; 546/70
(58) Field of Search .................. 514/284, 285, 514/280, 248; 544/233; 546/48, 70, 61

(56) References Cited

U.S. PATENT DOCUMENTS

| 2,985,661 A | 5/1961 | Hien et al. .................. 260/309 |
| RE26,065 E | 7/1966 | Marvel et al. ................ 260/47 |

(List continued on next page.)

FOREIGN PATENT DOCUMENTS

| EP | 0496634 | 7/1992 | ....... C07D/491/056 |
| GB | 2108955 | 5/1983 | |
| RU | 1530628 | 12/1989 | ......... C07D/235/20 |
| WO | 92/21661 | 12/1992 | ......... C07D/221/18 |
| WO | 97/29106 | 8/1997 | ......... C07D/455/02 |

OTHER PUBLICATIONS

Godowski, K.C., et al., USPATFULL Database, No. 95:20510, RN No. 218–38–2 (Benzo[c]phenanthradine), from U.S. Patent 5,395,615, 2 p., (Mar. 7, 1995).

Southard, G.L., et al., USPATFULL Database, No. 91:36238, RN No. 218–38–2 (Benzo[c]phenanthradine), from U.S. Patent 5,013,553, 2 p., (May 7, 1991).

Aquirre, J.M., et al., "Reaction of 1,2–diarylethylamides with ethyl polyphosphate(EPP): Correlation of the von Braun, Ritter and Bischler–Napieralski reactons", *Chemical Abstracts, 111* (*13*), Abstract No. 115004, pp. 25–27, (Sep. 25, 1989).

(List continued on next page.)

*Primary Examiner*—D. Margaret Seaman
(74) *Attorney, Agent, or Firm*—Schwegman, Lundberg, Woessner & Kluth, P.A.

(57) ABSTRACT

The present invention provides compounds of formula I:

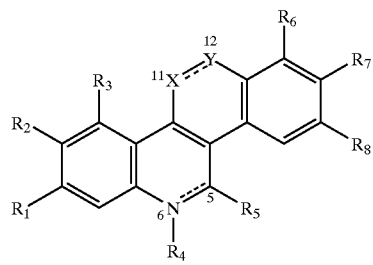

wherein the R substituents and atoms X and Y are as defined in specification. The present invention also provides pharmaceutical compositions and methods of inhibiting cancer cell growth.

26 Claims, 7 Drawing Sheets

U.S. PATENT DOCUMENTS

| | | | | |
|---|---|---|---|---|
| 3,449,330 A | 6/1969 | Guglielmetti et al. | ....... | 260/240 |
| 3,538,097 A | 11/1970 | Lowe et al. | ................ | 260/268 |
| 3,912,740 A | 10/1975 | Zee-Chang et al. | ......... | 260/286 |
| 4,749,708 A | 6/1988 | Maroko | ...................... | 514/284 |
| 4,761,417 A | 8/1988 | Maroko et al. | ............. | 514/282 |
| 4,938,949 A | 7/1990 | Borch et al. | ................... | 424/10 |
| 5,106,863 A | 4/1992 | Hajos et al. | ................ | 514/395 |
| 5,112,532 A | 5/1992 | Ninomiya et al. | .......... | 252/587 |
| 5,126,351 A | 6/1992 | Luzzio et al. | ............... | 514/291 |
| 5,153,178 A | 10/1992 | Maroko | ....................... | 514/26 |
| 5,244,903 A | 9/1993 | Wall et al. | .................. | 514/279 |
| 5,318,976 A | 6/1994 | Luzzi et al. | ................ | 514/279 |
| 6,140,328 A | * 10/2000 | LaVoie | | |

OTHER PUBLICATIONS

Arumugam, N., et al., "Synthesis of 7,8–Benzophenanthridines", *Indian Journal of Chemistry*, 12, pp. 664–667, (Jul. 1974).

Badia, D., et al., "Silicon–mediated isoquinoline synthesis: preparation and stereochemical characterization of 4–hydroxy–3–phenylisoquinolines", *Chemical Abstracts*, 117 (13), Abstract No. 131034, p. 730, (Sep. 28, 1992).

Baezner, C., et al., "Uberfuhrung von o–nitro– and o,p–dinitro–benzylchlorid in acridinderivate", *Berichte der Deutschen Chemischn Gessellschaft*, 39, pp. 2438–2447, (1906).

Bathini, Y., et al., "Covenient Routes to Substituted Benzimidazoles and Imidazolo[4,5–b]pyridines Using Nitrobenzene as Oxidant", *Synthetic Communications*, 20 (7), pp. 955–963, (1990).

Bhakuni, D.S., et al., "Protoberberine Alkaloids", *The Alkaloids*, V28, Chapter 2, Academic Press, Inc., pp. 95–181, (1986).

Bjornsti, M., et al., "Expression of Human DNA Topoisomerase I in Yeast Cells Lacking Yeast DNA Topoisomerase I: Restoration of Sensitivity of the Cells to the Antitumor Drug Camptothecin", *Cancer Research*, 49 (22), pp. 6318–6323, (Nov. 15, 1989).

Bradsher, C.K., et al., "α–Acyl–o–tolunitriles as intermediates in the preparation of 3–substitute isoquinolines and 1–amino–2–benzopyrylium derivatives", *Chemical Abstracts*, 089 (21), Abstract No. 179810, pp. 3817–3820, (1978).

Buu–Hoi, N., "The chemistry of carcinogenic nitrogen compounds. Part V. Angular hydroxybenzacridines and hydroxydibenzacridines", *Journal of the Chemical Society, Letchworth GB*, pp. 2096–2099, (1950).

Buu–Hoi, N., et al., "The chemistry of carcinogenic nitrogen compounds. Part X. The Pfitzinger reaction in the synthesis of 1:2 benzacridines", *Journal of the Chemical Society, Letchworth, GB*, pp. 279–281, (1952).

Chen, A.Y., et al., "A New Mammalian DNA Topoisomerase I Poison Hoechst 33342: Cytoxicity and Drug Resistance in Human Cell Cultures", *Cancer Research*, 53 (6), pp. 1332–1337, (Mar. 15, 1993).

Chen, A.Y., et al., "DNA Minor Groove–Binding Ligands: A Different Class of Mammalian DNA Topoisomerase I Inhibitors", *Proc. Natl. Acad. Sci., USA*, 90, pp. 8131–8135, (Sep. 1993).

Chen, A.Y., et al., "DNA Topoisomerases: Essential Enzymes and Lethal Targets", *Annu. Rev., Pharmacol. Toxicol.*, 34, pp. 191–218, (1994).

Cherif, A., et al., "N–(5,5–Diacetoxypent–l–yl)doxorubicin: A New Intensely Potent Doxorubicin Analogue", *J. Med. Chem.*, 35, pp. 3208–3214, (1992).

Croisy, M., et al., "Synthesis and Carcinogenic Activity of Oxidized Benzacridines: Potential Metabolites of the strong carcinogen 7–Methylbenz[c] acridine and of the inactive isomer 12–methylbenz[a]acridine", *J. Med. Chem*, 26, pp. 303–306, (1983).

D'arpa, P., et al., "Topoisomerase–Targeting Antitumor Drugs", *Biochimica et Biophysica Acta*, 989, pp. 163–177, (1989).

Dominguez, E., et al., "Dehydrogenation reactions of 1–substituted–3–aryltetrahydroisoquin oline derivatives", *Chemical Abstracts*, 101 (11), Abstract No. 090742, pp. 525–528, (1984).

Dorofeenko, G.N., et al., "Synthesis of 3–aryl derivatives of 2–benzopyrylium salts with free.alpha–positions", *Chemical Abstracts*, 074 (15), Abstract No. 076295, pp. 1013–1014, (1971).

Fitzgerald, J.J., et al., "Reaction of benzocyclobutene oxides with nitriles: synthesis of hypecumine and other 3–substituted isoquinolines", *Chemical Abstracts*, 122 (7), Abstract No. 081704, p. 1128, (Feb. 13, 1995).

Fox, G.J., et al., "Para–Bromination of Aromatic Amines: 4–Bromo–N, N–Dimethyl–3–(Trifluoromethyl)Aniline", *Organic Synthesis*, 55, pp. 20–23, (1973).

Fujii, N., et al., "Induction of Mammalian DNA Topoisomerase I–mediated DNA Cleavage and DNA Winding by Bulgarein", *Journal of Biological Chemistry*, 268, pp. 13160–13165, (1993).

Gallo, R.C., et al., "Studies on the Antitumor Activity, Mechanism of Action, and Cell Cycle Effects of Camptothecin", *Journal of the National Cancer Institute*, 46, pp. 789–795, (Apr. 1971).

Gandhi, K.K., et al., "Regioselective thermal cyclization of 3–substituted arylenaminoimine hydrochlorides, a convenient method for the synthesis of functionalized polycyclic quinoline derivatives", *Heterocycles*, 41 (5), pp. 911–920, (1995).

Gapinath, K.W., et al., "Synthesis of Some 1:2– and 7:8–Benzophenanthridines", *Journal of the Chemical Society*, 1958, pp. 504–509, (1958).

Garcia, A., et al., "A simple direct approact to 1–substituted 3–arylisoquinolines from deoxybenzoins and nitriles", *Chemical Abstracts*, 110 (25), Abstract No. 231407, pp. 6681–6686, (Jun. 19, 1989).

Gatto, B., et al., "Identification of Topoisomerase I as the Cyctotoxic Target of the Protoberberine Alkaloid Coralyne", *Cancer Research*, 56, pp. 2795–2800, (1996).

Giovanella, B.C., et al., "Complete Growth Inhibition of Human Cancer Xenografts in Nude Mice by Treatment with 20–(S)—Campothecin", *Cancer Research*, 51, pp. 3052–3055, (Jun. 1, 1991).

Goldman, G.H., et al., "Differential poisoning of humand and aspergilus nidulans DNA topoisomeras I by Bi– Terbenzimidazoles", *Biochemistry*, 36 (21), pp. 6488–6494, (1997).

Hahn, F.E., et al., "Berberine", *In: Antibiotics, Mechanism of Action of Antimicrobial and Antitumor Agents*, vol. III, J.W. Corcoran, et al., (eds.), Springer–Verlag, pp. 577–584, (1975).

Halligan, B.D., et al., "Purification and Characterization of a Type II DNA Topoisomerase from Bovine Calf Thymus", *The Journal of Biological Chemistry*, 260 (4), pp. 2475–2482, (1985).

Hoan, N., et al., "Syntheses from o–halogenated anisoles and phenetoles", *Chemical Abstracts*, 41 (20), Abstract No. 6571bg, 1 p., (1947).

Hsiang, Y., et al., "Identification of Mammalian DNA Topoisomerase I as an Intracellular Target of the Anticancer Drug Camptothecin", *Cancer Research*, 48 (7), pp. 1722–1726, (Apr. 1, 1988).

Iwao, M., et al., "A Regiospecific Synthesis of Carbazones via Consecutive Palladium–Catalyzed Cross–coupling and Aryne–Mediated Cyclization", *Heterocycles*, 36, pp. 1483–1488, (1993).

Janin, Y.L., et al., "Synthesis and Evaluation of New 6–Amino–Substituted Benzo[c]phenanthridine Derivatives", *J. Med. Chem*, 36 (23), pp. 3686–3692, (1993).

Kametani, T., et al., "Studies on the synthesis of heterocyclic compounds. DCXXVII. The formation of 2,3,9,10–tetramethoxybenz[c]acridine by treatment of 6,7–dimethoxy–1–(4,5–dimethoxy–2–nitrophenethyl)–2methylisoquinoline with triethyl phosphite", *Chemical and Pharmaceutical Bulletin*, 23 (9), pp. 2025–2028, (1975).

Kessar, S.V., et al., "Azasteroids. Part VII. Synthesis of 7–hydroxy–2–methoxy–7,8,9,10–tetrahydrobenzo[i]phenanthridine", *J. Chem Soc.*, pp. 259–261, (1971).

Kessar, S.V., et al., "New Routes to Condensed Polynuclear Compounds: Part X–Synthesis of Some Benzo[i]phenanthridines through Benzyne Cyclization", *Indian Journal of Chemistry*, 11, pp. 624–627, (Jul. 1973).

Kim, J.S., et al., "Influence of steric factors on topoisomerase I inhibition and cytotoxicity of bisbenzimidazoles related to Hoechst 33342", *Proceedings of the 86th Annual Meeting of the American Association for Cancer Research*, 36, Abstract No. 2689, Toronto, Ontario, Canada, p. 451, (Mar. 1995).

Kim, J.S., et al., "Quantitative structure–activity relationships on 5–substituted terbenzimidazoles as topoisomerase I poisons and antitumor agents", *Bioorg. Med. Chem.*, 6 (2), pp. 163–172, (1998).

Kim, J.S., et al., "Steric factors associated with the topoisomerase I inhibition and cytotoxicity of substituted bisbenzimidazoles", *Abstract 10– Proceedings of the American Association of Pharmaceutical Scientists Eastern Regional Meeting*, p. 27, (1995).

Kim, J.S., et al., "Structure–activity Relationships of Benzimidazoles and Related Heterocycles as Topoisomerase I Poisons", *Bioorganic & Med. Chem.*, 4, pp. 621–630, (1996).

Kim, J.S., et al., "Substituted 2,5'–Bi–1H–benzimidazoles: Topoisomerase I Inhibition and Cytotoxicity", *J. Med. Chem.*, 39, pp. 992–998, (1996).

Kim, J.S., et al., "Terbenzimidazoles: influence of 2"–, 4–, and 5–substituents on cytotoxicity and relative potency as topoisomerase I poisons", *J. Med. Chem.*, 40, 2818–2821, (1997).

Kitamura, T., et al., "Isoquinoline derivatives from the Ritter–type reaction of vinyl cations", *Chemical Abstracts*, 102 (1), Abstract No. 006157, pp. 1351–1354, (Jan. 7, 1985).

Knab, A.M., et al., "Mechanisms of Camptothecin Resistance in Yeast DNA Topoisomerase I Mutants", *The Journal of Biological Chemistry*, 268 (30), pp. 22322–22330, (1993).

LaVoie, E.J., et al., "Structure–activity studies related to minor groove–binding ligands which inhibit mammalian DNA topoisomerase I", *Abstract 1—Proceedings of the 85th Annual Meeting of American Association for Cancer Research*, San Francisco, CA, p. 2699, (Apr. 1994).

Liu, L.F., et al., "Cleavage of DNA by Mammalian DNA by Mammalian DNA Topoisomerase II", *The Journal of Biological Chemistry*, 258 (24), pp. 15365–15370, (1983).

Makhey, D., et al., "Coralyne and Related Compounds as Mammalian Topoisomerase I and Topoisomerase II Poisons", *Biorg. & Med. Chem. Lett.*, 4, pp. 781–791, (1996).

Makhey, D., et al., "Protoberberine Alkaloids and Related Compounds as Dual Inhibitors of Mammalian Topoisomerase I and II", *Med Chem. Res.*, 5, pp. 1–12, (1994).

Meegalla, S.K., et al., "Synthesis and Pharmacological Evaluation of Isoindolo[1,2–b]quinazolinone and Isoindolo[2,1–a]benzimidazole Derivatives Related to the Antitumor Agent Batracylin", *J. Med. Chem.*, 37, pp. 3434–3439, (1994).

Memetzidis, G., et al., "Structure–affinity relationships of berbines or 5,6,13,13a–tetrahydro–8H–dibenzo[a,g]quinolizines at.alpha.–adrenoceptors", *Eur. J. Med. Chem.*, 26, pp. 605–611, (1991).

Mohanty, M., et al., "New Therapeutic agents of the quinoline series. I. Fused quinolyl compounds", *Chemical Abstracts*, 69 (5), p. 1792, (Jul. 29, 1968).

Nelson, J.T., et al., "Proton and carbon–13 NMR spectra of fifteen substituted isoquinolines", *Chemical Abstracts*, 115 (5), Abstract No. 048721, 1 p., (Aug. 5, 1991).

Peters, D., et al., "Synthesis of Various 5–Substituted Uracils", *J. Heterocyclic Chem.*, 27, pp. 2165–2173, (Nov./Dec. 1990).

Pilch, D.S., et al., "Biophysical Characterization of a Cytotoxic, Topoisomerase I Poison", *Abstract 8—Proceedings of the 3rd Annual Scientific Retreat of the Cancer Institute of New Jersey*, Princeton Marriott Forrestal Village, Princeton, NJ, p. 3, (Jun. 1, 1995).

Piper, J.R., et al., "Synthesis and Antifolate Activity of 5–Methyl–5,10–dideaza Analogues of Aminopterin and Folic Acid and an Alternative Synthesis of 5,10–Dideazatetrahydrofolic Acid, a Potent Inhibitor of Glycinamide Ribonucleotide Formyltransferase", *J. Med. Chem.*, 31, pp. 2164–2169, (1988).

Porai–Koshits, B.A., et al., "Imadazole derivatives Synthesis of some polybenzimidazoles", *J. Gen. Chem. USSR*, 23, As related in Chemical Abstracts, 48 (10) (1954), Col. 12740, pp. 873–879, (1953).

Porai–Koshits, B.A., et al., "Imidazole derivatives. Synthesis of some polybenzimidazoles", *Zhur, Obshchei Khim*, 23, As related in Chemical Abstracts, 48 (1954) Col. 4523, pp. 835–841, (1953).

Quast, U., et al., "Heterocyclic.alpha.–carbinolamines with theisoquinuclidine skeleton. 3. Benzoisoquinuclidines", *Chemical Abstracts*, 097 (21), Abstract No. 182180, pp. 1501–1508, (1982).

Safaryan, G.P., et al., "2–Benzopyrylium salts. 25, Reaction of 2–benzopyrylium salts with some nucleophiles", *Chemical Abstracts*, 096 (17), Abstract No. 142656, pp. 1608–1611, (1982).

Schiess, P., et al., "Thermolytic ring opening of acyloxybenzocyclobutenes: an efficient route to 3–substituted isoquinolines", *Chemical Abstracts*, 104 (19), Abstract No. 168332, pp. 3959–3962, (May 12, 1986).

Shcherbakova, I.V., et al., "2–Benzopyrilium salts.35.Synthesis of the natural alkaloid dehydronorocoralydine and other substituted salts of dibenzo[a,g] quinolizine", *Chemical Abstracts, 112* (*19*), Abstract No. 179554, pp. 75–80, (May 7, 1990).

Singh, M.P., et al., "Synthesis and Sequence–Specific DNA Binding of a Topoisomerase Inhibitory Analog of Hoechst 33258 Designed for Altered Base and Sequence Recognition", *Chem. Res. Toxicol., 5,* pp. 597–607, (1992).

Sotomayor, N., et al., "Oxidation reactions of 2'–functionalized 3–aryltetrahydro and 3,4–dihydroisoquinolines", *Chemical Abstracts, 124* (*11*), Abstract No. 145854, p. 1227, (Mar. 11, 1996).

Stermitz, F.R., et al., "Synthesis and Biological Activity of Some Antitumor Benzophenanthridinum Salts", *Journal of Medicinal Chemistry, 18,* pp. 708–713, (1975).

Sun, Q., et al., "Structure activity of novel topoisomerase I inhibitors related to Hoechst 33342", *Abstract 6—Proceedings of the American Association of Pharmaceutical Scientists Eastern Regional Meeting,* Hyatt Regency Hotel, New Brunswick, NJ, p. 25, (Jun. 5–6, 1995).

Sun, Q., et al., "Structure Activity of Topoisomerase I Poisons Related to Hoechst 33342", *Bioorganic & Medicinal Chemistry Letters, 4* (*24*), pp. 2871–2876, (1994).

Sun, Q., et al., "Structure–activity studies related to minor groove–binding ligands which inhibit mammalian DNA topoisomerase I", *Cancer Institute of New Jersey's First Annual Scientific Retreat, Abstract 2,* Princeton Marriott Forrestal Village, Princeton, NJ, p. 66, (Jun. 7, 1994).

Sun, Q., et al., "Synthesis and Evaluation of Terbenzimidazoles as Topoisomerase I Inhibitors", *Chemical Abstracts, 123* (*15*), Abstract No. 198740r, p. 1241, (1995).

Sun, Q., et al., "Synthesis and pharmacological evaluation of a series of novel DNA topoisomerase I inhibitors as antitumor agents", *Proceedings of the 86th Annual Meeting of the American Association for Cancer Research,* Toronto, Ontario, Canada, p. 2688, (1995).

Sun, Q., et al., "Synthesis and Pharmacological Evaluation of a Series of Novel DNA Topoisomerase I Inhibitors as Antitumor Agents", *Scientific Proceedings of 86th Annual Meeting of the American Association for Cancer Research, Abstract 3,* Toronto, Canada, 1 p., (Mar. 18–22, 1995).

Sun. Q., et al., "Synthesis of Benzimidazo[2,1–a]isoquinolines and 5,6–Dihydrobenzimidazo[2,1–a]isoquinolines", *Syn. Lett., submitted,* Paper No. 7, 6 p., (1995).

Sun, S., et al., "Synthesis and Evaluation of Terbenzimidazoles as Topoisomerase I Inhibitors", *J. Med. Chem, 38,* pp. 3638–3644, (1995).

Walterova, D., et al., "Isolation, Chemistry and Biology of Alkaloids from plants of Papaveraceae. Part XCV. Practical application of isotachophoresis in analysis of isoquinoline alkaloids", *Chemical Abstracts, 104* (*12*), pp. 23–36, (1986).

Wang, L., et al., "Inhibition of Topoisomerase I Function by Coralyne and 5,6–Dihydrocoralyne", *Chem. Res. Toxicol., 9,* pp. 75–83, (1996).

Wang, L., et al., "Inhibition of Topoisomerase I Function by Nitidine and Fagaronine", *Chem. Res. Toxicol, 6,* pp. 813–818, (1993).

Yadagiri, B., et al., "Convenient Routes to Substituted Benzimidazoles and Imidazolo[4,5–b]Pyridines Using Nitrobenzene as Oxidant", *Synthetic Communications, 20* (*7*), pp. 955–963, (1990).

Yamamoto, Y., et al., "Reaction of 6H–1, 3–oxazin–6–one with benzyne giving isoquinoline derivatives", *Chemical Abstracts, 118* (*1*), Abstract No. 059563, 2 p., (Feb. 15, 1993).

Yamashita, Y., et al., "Induction of Mammalian DNA Topoisomerase I and II Mediated DNA Cleavage by Saintopin, and New Antitumor Agent from Fungus", *Biochemistry, 30,* pp. 5838–5845, (1991).

Yamashita, Y., et al., "Induction of Mammalian DNA Topoisomerase I Mediated DNA Cleavage by Antitumor Indolocarbazole Derivatives", *Biochemistry, 31,* pp. 12069–12075, (1992).

\* cited by examiner

4

5

6

7

27

28

HETEROCYCLIC CYTOTOXIC AGENTS

This is a 371 of PCT/US98/26292, filed Dec. 11, 1998 which is a continuation of Ser. No. 08/989,576, filed Dec. 13, 1997, U.S. Pat. No. 6,140,329.

GOVERNMENT FUNDING

The invention described herein was made with government support under grant CA 39662 awarded by the National Cancer Institute. The United States Government has certain rights in the invention.

BACKGROUND OF THE INVENTION

DNA-topoisomerases are enzymes which are present in the nuclei of cells where they catalyze the breaking and rejoining of DNA strands, which control the topological state of DNA. Recent studies also suggest that topoisomerases are also involved in regulating template supercoiling during RNA transcription. There are two major classes of mammalian topoisomerases. DNA-topoisomerase-1 catalyzes changes in the topological state of duplex DNA by performing transient single-strand breakage-union cycles. In contrast, mammalian topoisomerase II alters the topology of DNA by causing a transient enzyme bridged double-strand break, followed by strand passing and resealing. Mammalian topoisomerase II has been further classified as Type II α and Type II β. The antitumor activity associated with agents which are topoisomerase poisons is associated with their ability to stabilize the enzyme-DNA cleavable complex. This drug-induced stabilization of the enzyme-DNA cleavable complex effectively converts the enzyme into a cellular poison.

Several antitumor agents in clinical use have potent activity as mammalian topoisomerase II poisons. These include adriamycin, actinomycin D, daunomycin, VP-16, and VM-26 (teniposide or epipodophyllotoxin). In contrast to the number of clinical and experimental drugs which act as topoisomerase II poisons, there are currently only a limited number of agents which have been identified as topoisomerase I poisons. Camptothecin and its structurally-related analogs are among the most extensively studied topoisomerase I poisons. Recently, bi- and terbenzimidazoles (Chen et al., *Cancer Res.* 1993, 53, 1332–1335; Sun et al., *J. Med. Chem.* 1995, 38, 3638–3644; Kim et al., *J. Med. Chem.* 1996, 39, 992–998), certain benzo[c]phenanthridine and protoberberine alkaloids and their synthetic analogs (Makhey et al., *Med. Chem. Res.* 1995, 5, 1–12; Janin et al., *J. Med. Chem* 1975, 18, 708–713; Makhey et al., *Bioorg. & Med. Chem.* 1996, 4, 781–791), as well as the fungal metabolites, bulgarein (Fujii et al., *J. Biol. Chem.* 1993, 268, 13160–13165) and saintopin (Yamashita et al., *Biochemistry* 1991, 30, 5838–5845) and indolocarbazoles (Yamashita et al., *Biochemistry* 1992, 31, 12069–12075) have been identified as topoisomerase I poisons.

The exceptional topoisomerase poisoning observed with coralyne, nitidine, 5,6-dihydro-8-desmethylcoralyne and related analogs prompted several recent studies on those structural features which are associated with their ability to act specifically as poisons of topoisomerase I or topoisomerase II (Gatto et al., *Cancer Res.* 1996, 56, 2795–2800; Wang et al., *Chem. Res. Toxicol.* 1996, 9, 75–83; Wang et al., *Chem. Res. Toxicol.,* 1993, 6, 813–818). A common feature associated with all three of these agents is the presence of a 3-phenylisoquinolinium moiety within their structure.

Despite the observation that several of these compounds had similar potency to camptothecin as a topoisomerase I poison or similar potency to VM-26 as a topoisomerase II poison, they possessed only modest cytotoxic activity. The absence of a more direct correlation with their potency as topoisomerase poisons was attributed, in part, to the likelihood that these agents are not likely to be absorbed as effectively into cells as either camptothecin or VM-26. The presence of the quaternary ammonium group most likely impedes cellular uptake. It has been speculated that agents such as coralyne and nitidine may need to undergo hydrolysis to permit effective transport, with subsequent dehydration or cyclodehydration to reform the quaternary ammonium parent compound. This may explain the relatively poor antitumor activity observed in vivo with agents such as coralyne or nitidine.

Presently, a need exists for novel anti-cancer agents, for anti-cancer agents that exhibit improved activity, and for anti-cancer agents that exhibit fewer side-effects or improved selectivity compared to existing agents.

SUMMARY OF THE INVENTION

The present invention provides compounds that show inhibitory activity against topoisomerase I and/or topoisomerase II, and compounds that are effective cytotoxic agents against cancer cells, including drug-resistant cancer cells. Accordingly, the invention provides a compound of the invention which is a compound of formula I:

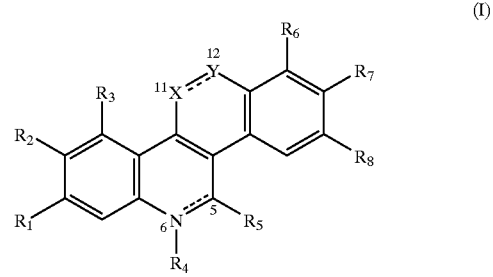

wherein

R$_1$, R$_2$, and R$_3$ are each individually hydrogen, (C$_1$–C$_6$)alkyl, (C$_3$–C$_6$)cycloalkyl, (C$_1$–C$_6$)alkoxy, nitro, hydroxy, NR$_g$R$_h$, COOR$_k$, OR$_m$, or halo; or R$_1$ and R$_2$ taken together are methylenedioxy and R$_3$ is hydrogen, (C$_1$–C$_6$)alkyl, (C$_3$–C$_6$)cycloalkyl, (C$_1$–C$_6$)alkoxy, nitro, hydroxy, NR$_g$R$_h$, COOR$_k$, OR$_m$, or halo; or R$_2$ and R$_3$ taken together are methylenedioxy and R$_1$ is hydrogen, (C$_1$–C$_6$)alkyl, (C$_3$–C$_6$)cycloalkyl, (C$_1$–C$_6$)alkoxy, nitro, hydroxy, NR$_g$R$_h$, COOR$_k$, OR$_m$, or halo;

R$_4$ is oxy, (C$_1$–C$_6$)alkyl, or is absent;

R$_5$ is hydrogen, hydroxy, or (C$_1$–C$_6$)alkyl;

R$_6$, R$_7$ and R$_8$ are each individually hydrogen, (C$_1$–C$_6$)alkyl, (C$_3$–C$_6$)cycloalkyl, (C$_1$–C$_6$)alkoxy, nitro, hydroxy, NR$_g$R$_h$, COOR$_k$, OR$_m$, or halo; or R$_6$ and R$_7$ taken together are methylenedioxy and R$_8$ is hydrogen, (C$_1$–C$_6$)alkyl, (C$_3$–C$_6$)cycloalkyl, (C$_1$–C$_6$)alkoxy, nitro, hydroxy, NR$_g$R$_h$, COOR$_k$, OR$_m$, or halo; or R$_7$ and R$_8$ taken together are methylenedioxy and R$_6$ is hydrogen, (C$_1$–C$_6$)alkyl, (C$_3$–C$_6$)cycloalkyl, (C$_1$–C$_6$)alkoxy, nitro, hydroxy, NR$_g$R$_h$, C(=O)R$_k$, COOR$_k$, OR$_m$, or halo;

each bond represented by ——— is individually present or absent;

X is C(R$_a$)(R$_b$) or NR$_c$;

Y is C(R$_d$)(R$_e$) or NR$_f$;

if present, $R_a$ and $R_b$ are each independently hydrogen or $(C_1-C_6)$alkyl if the bond between the 11- and 12-positions represented by ———— is absent; or $R_a$ is hydrogen or $(C_1-C_6)$alkyl and $R_b$ is absent if the bond between the 11- and 12-positions represented by ———— is present;

if present, $R_c$ and $R_f$ are each independently hydrogen or $(C_1-C_6)$alkyl if the bond between the 11- and 12-positions represented by ———— is absent; or $R_c$ and $R_f$ are each independently $(C_1-C_6)$alkyl or absent if the bond between the 11- and 12-positions represented by ———— is present;

if present, $R_d$ and $R_e$ are each independently hydrogen or $(C_1-C_6)$alkyl if the bond between the 11- and 12-positions represented by ———— is absent; or $R_d$ is hydrogen or $(C_1-C_6)$alkyl and $R_e$ is absent if the bond between the 11- and 12-positions represented by ———— is present;

each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and each $R_m$ is independently $(C_1-C_6)$alkanoyl, aryl, or aryl $(C_1-C_6)$alkyl;

wherein any $(C_1-C_6)$alkyl, $(C_3-C_6)$cycloalkyl, or $(C_1-C_6)$ alkoxy of $R^1$, $R^2$, $R^3$, $R^6$, $R^7$, $R^8$, or $R_k$ is optionally substituted on carbon with 1, 2, or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$ alkanoyl; or $R_n$ and $R_p$ together with the nitrogen to which they are attached are pyrrolidino, piperidino, morpholino, or thiomorpholino;

wherein any aryl is optionally be substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$ alkoxy;

provided that at least one of $R_2$ and $R_8$ is hydrogen, methyl, nitro, hydroxy, amino, fluoro or chloro; or at least one of $R_2$ and $R_8$ forms part of a methylenedioxy; and provided that $R_1-R_3$ and $R_6-R_8$ are not all hydrogen;

or a pharmaceutically acceptable salt thereof.

The invention also provides a pharmaceutical composition comprising a effective amount of a compound of formula I, or a pharmaceutically acceptable salt thereof, in combination with a pharmaceutically acceptable diluent or carrier.

The invention also provides a method of inhibiting cancer cell growth, comprising administering to a mammal afflicted with cancer, an amount of a compound of formula (I), effective to inhibit the growth of said cancer cells.

The invention also provides a method comprising inhibiting cancer cell growth by contacting said cancer cell in vitro or in vivo with an amount of a compound of claim 1, effective to inhibit the growth of said cancer cell.

The invention also provides a compound of formula I for use in medical therapy (preferably for use in treating cancer, e.g. solid tumors), as well as the use of a compound of formula I for the manufacture of a medicament useful for the treatment of cancer, e.g. solid tumors.

The invention also provides processes and novel intermediates disclosed herein which are useful for preparing compounds of the invention. Some of the compounds of formula I are useful to prepare other compounds of formula I.

DETAILED DESCRIPTION

Figure 1:
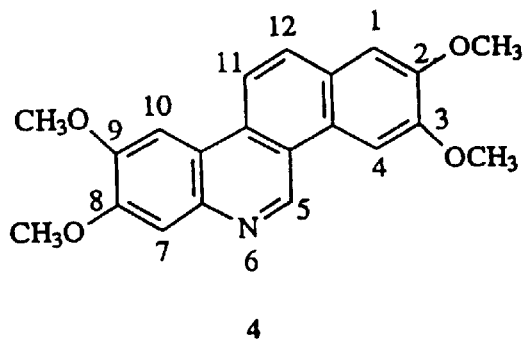
FIG. 1 shows the structure of representative compounds of the invention(6, 7, 27, 28) and other compounds (4 and 5).
Figure 1:
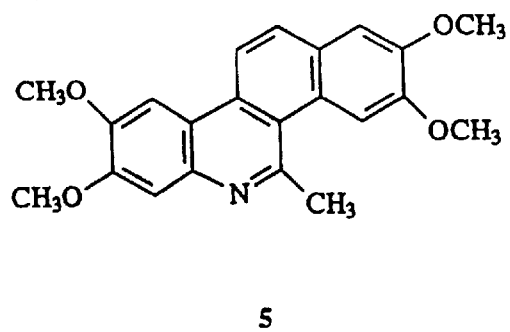
Figure 1:
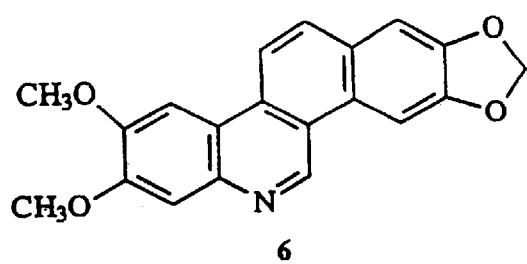
Figure 1:
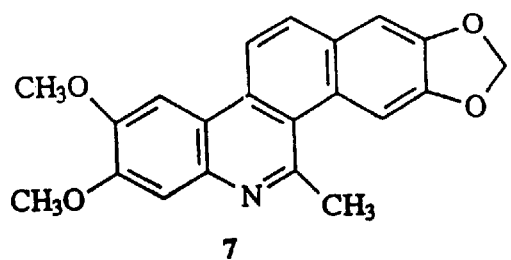
Figure 1:
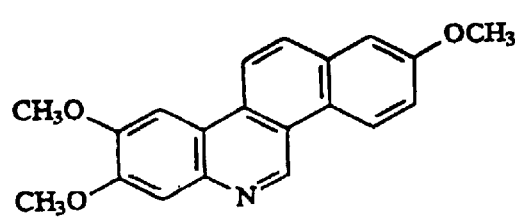
Figure 1:
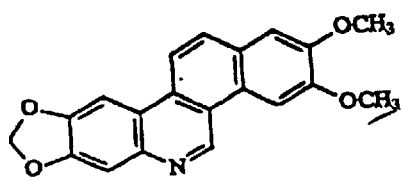

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine topoisomerase poisioning activity or cytotoxicity using the standard tests described herein, or using other similar tests which are well known in the art.

Specific values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl, butanoyl, pentanoyl, or hexanoyl; and aryl can be phenyl, indenyl, or naphthyl;.

Specifically, $R_2$ or $R_7$ can be hydroxy, methoxy, benzyloxy, amino, hydroxymethyl, aminomethyl, aminocarbonyl, methoxycarbonyl, trifluoromethyl, 3-aminopropoxycarbonyl, or 2-hydroxyethyl.

Specifically, $R_3$ can be hydrogen.

Specifically, $R_4$ can be absent; or $R_4$ can be $(C_1–C_6)$alkyl.

Specifically, $R_5$ can be methyl or hydrogen.

A specific group of compounds are compounds of formula I wherein $R_1$, $R_2$ and $R_3$ are each individually hydrogen, or $(C_1–C_6)$alkoxy; or $R_1$ and $R_2$ taken together are methylenedioxy (—OCH$_2$O—) and $R_3$ is hydrogen or $(C_1–C_6)$)alkoxy; or a pharmaceutically acceptable salt thereof.

Another specific group of compounds are compounds of formula I wherein: $R_1$, $R_2$ and $R_3$ are each individually hydrogen, $(C_1–C_6)$alkyl, $(C_3–C_6)$cycloalkyl, $(C_1–C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1–C_6)$alkyl, $(C_3–C_6)$cycloalkyl, $(C_1–C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1–C_6)$alkyl, $(C_3–C_6)$cycloalkyl, $(C_1–C_6)$alkoxy, nitro, hydroxy, $NR_gR_h$, $COOR_k$, $OR_m$, or halo; $R_4$ is oxy, $(C_1–C_6)$alkyl, or is absent; $R_5$ is hydrogen, hydroxy, or $(C_1–C_6)$alkyl; $R_6$, $R_7$ and $R_8$ are each individually hydrogen, $(C_1–C_6)$alkyl, $(C_3–C_6)$cycloalkyl, $(C_1–C_6)$alkoxy, nitro, hydroxy, $NR_gR_h$, $COOR_k$, $OR_m$, or halo; or $R_6$ and $R_7$ taken together are methylenedioxy and $R_8$ is hydrogen, $(C_1–C_6)$alkyl, $(C_3–C_6)$cycloalkyl, $(C_1–C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1–C_6)$alkyl, $(C_3–C_6)$cycloalkyl, $(C_1–C_6)$alkoxy, nitro, hydroxy, $NR_gR_h$, $COOR_k$, $OR_m$, or halo; each bond represented by ——— is individually present or absent; X is $C(R_a)(R_b)$ or $NR_c$; Y is $C(R_d)(R_e)$ or $NR_f$; if present, $R_a$ and $R_b$ are each independently hydrogen or $(C_1–C_6)$alkyl if the bond between the 11- and 12-positions represented by ——— is absent; or $R_a$ is hydrogen or $(C_1–C_6)$alkyl and $R_b$ is absent if the bond between the 1- and 12-positions represented by ——— is present; if present, $R_a$ and $R_f$ are each independently hydrogen or $(C_1–C_6)$alkyl if the bond between the 11- and 12-positions represented by ——— is absent; or $R_a$ and $R_f$ are each independently $(C_1–C_6)$alkyl or absent if the bond between the 11- and 12-positions represented by ——— is present; if present, $R_d$ and $R_e$ are each independently hydrogen or $(C_1–C_6)$alkyl if the bond between the 11- and 12-positions represented by ——— is absent; or $R_d$ is hydrogen or $(C_1–C_6)$alkyl and $R_e$ is absent if the bond between the 11- and 12-positions represented by ——— is present; each $R_g$ and $R_h$ is independently hydrogen, $(C_1–C_6)$alkyl, $(C_3–C_6)$cycloalkyl, $(C_1–C_6)$alkoxy, $(C_1–C_6)$alkanoyl, aryl, aryl$(C_1–C_6)$alkyl, aryloxy, or aryl$(C_1–C_6)$alkoxy; or $R_g$ and $R_h$ together with the nitrogen to which they are attached are pyrrolidino, piperidino, morpholino, or thiomorpholino; each $R_k$ is independently hydrogen, or $(C_1–C_6)$alkyl; and each $R_m$ is independently $(C_1–C_6)$alkanoyl, aryl, or aryl$(C_1–C_6)$)alkyl; provided that at least one of $R_2$ and $R_8$ is hydrogen, methyl, nitro, hydroxy, amino, fluoro or chloro; or at least one of $R_2$ and $R_8$ forms part of a methylenedioxy; and provided that $R_1$–$R_3$ and $R_6$–$R_8$ are not all hydrogen; or a pharmaceutically acceptable salt thereof.

Another specific group of compounds are compounds of formula I wherein $R_7$ or $R_8$ is $(C_1–C_6)$alkoxy; or $R_7$ and $R_8$ taken together are methylenedioxy; or a pharmaceutically acceptable salt thereof.

Another specific group of compounds are compounds of formula I wherein $R_7$ and $R_8$ taken together are methylenedioxy; or a pharmaceutically acceptable salt thereof.

Another specific group of compounds are compounds of formula I wherein the bonds represented by ——— are both present; or a pharmaceutically acceptable salt thereof.

Another specific group of compounds are compounds of formula I wherein the bond between the 5- and the 6-positions that is represented by ——— is absent; or a pharmaceutically acceptable salt thereof.

Another specific group of compounds are compounds of formula I wherein the bond between the 11- and the 12-positions that is represented by ——— is absent; or a pharmaceutically acceptable salt thereof.

Another specific group of compounds are compounds of formula I wherein the bonds represented by ——— are both absent; or a pharmaceutically acceptable salt thereof.

Another specific group of compounds are compounds of formula I wherein X is $NR_c$; Y is $NR_f$; and $R_c$ and $R_f$ are each hydrogen or $(C_1–C_6)$alkyl if the bond between the 11- and 12-positions represented by ——— is absent; or $R_c$ and $R_f$ are each $(C_1–C_6)$alkyl or absent if the bond between the 11- and 12-positions represented by ——— is present; or a pharmaceutically acceptable salt thereof.

Another specific group of compounds of formula I, are compounds of formula III:

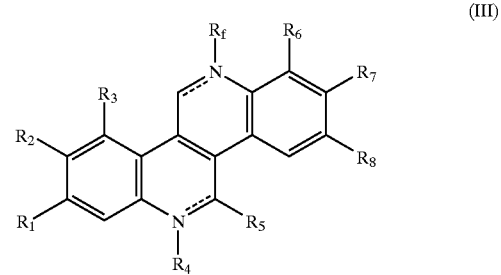

(III)

wherein $R_1$–$R_8$ are defined as hereinabove for the corresponding radical in a compound of formula I; each bond represented by ——— is individually present or absent; and $R_f$ is hydrogen or $(C_1–C_6)$alkyl if the bond between the 11- and 12-positions represented by ——— is absent; or $R_f$ is $(C_1–C_6)$alkyl or absent if the bond between the 11- and 12-positions represented by ——— is present; or a pharmaceutically acceptable salt thereof.

Another specific group of compounds of formula I, are compounds of formula IV:

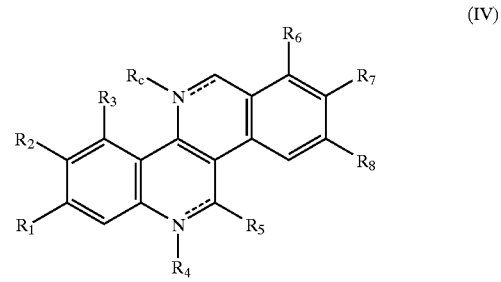

(IV)

wherein $R_1$–$R_8$ are defined as hereinabove for the corresponding radical in a compound of formula I; each bond represented by ——— is individually present or absent; and $R_c$ is hydrogen or $(C_1–C_6)$alkyl if the bond between the 11- and 12-positions represented by ——— is absent; or $R_c$ is $(C_1–C_6)$alkyl or absent if the bond between the 11- and 12-positions represented by ——— is present; or a pharmaceutically acceptable salt thereof Another specific group of compounds are compounds of formula I wherein $R_1$ is $(C_1-C_6)$alkoxy, nitro, hydroxy, or halo; or $R_1$ and $R_2$ taken together are methylenedioxy; or a pharmaceutically acceptable salt thereof.

Another specific group of compounds are compounds of formula I wherein $R_2$ is $(C_1-C_6)$alkoxy, nitro, hydroxy, or halo; or a pharmaceutically acceptable salt thereof.

Another specific group of compounds are compounds of formula I wherein $R_3$ is $(C_1-C_6)$alkoxy, nitro, hydroxy, or halo; or $R_2$ and $R_3$ taken together are methylenedioxy; or a pharmaceutically acceptable salt thereof.

Another specific group of compounds are compounds of formula I wherein $R_8$ is $(C_1-C_6)$alkoxy, nitro, hydroxy or halo; or $R_7$ and $R_8$ taken together are methylenedioxy; or a pharmaceutically acceptable salt thereof.

Another specific group of compounds are compounds of formula I wherein $R_7$ is $(C_1-C_6)$alkoxy, nitro, hydroxy, or halo; or a pharmaceutically acceptable salt thereof.

Another specific group of compounds are compounds of formula I wherein $R_6$ is $(C_1-C_6)$alkoxy, nitro, hydroxy, or halo; or $R_6$ and $R_7$ taken together are methylenedioxy; or a pharmaceutically acceptable salt thereof.

A preferred compound of the invention is a compound of formula I:

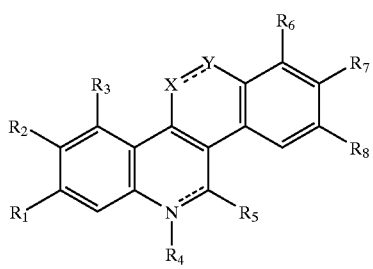

(I)

wherein $R_6$ $R_2$ and $R_3$ are each individually hydrogen, $(C_1-C_6)$alkyl, $(C_3-C_6)$cycloalkyl, $(C_1-C_6)$alkoxy, nitro, hydroxy, or halo; or $R_1$ and $R_2$ taken together are methylenedioxy ($-OCH_2O-$) and $R_3$ is hydrogen, $(C_1-C_6)$alkyl, $(C_3-C_6)$cycloalkyl, $(C_1-C_6)$alkoxy, nitro, hydroxy, or halo; or $R_2$ and $R_3$ taken together are methylenedioxy ($-OCH_2O-$) and $R_1$ is hydrogen, $(C_1-C_6)$alkyl, $(C_3-C_6)$cycloalkyl, $(C_1-C_6)$alkoxy, nitro, hydroxy or halo;

$R_4$ is oxy (forming an amine oxide), $(C_1-C_6)$alkyl, or is absent;

$R_5$ is hydrogen, hydroxy, or $(C_1-C_6)$alkyl;

$R_6$, $R_7$ and $R_8$ are each individually hydrogen, $(C_1-C_6)$alkyl, $(C_3-C_6)$cycloalkyl, $(C_1-C_6)$alkoxy, nitro, hydroxy, or halo; or $R_6$ and $R_7$ taken together are methylenedioxy ($-OCH_2O-$) and $R_8$ is hydrogen, $(C_1-C_6)$alkyl, $(C_3-C_6)$cycloalkyl, $(C_1-C_6)$alkoxy, nitro, hydroxy, or halo; or $R_7$ and $R_8$ taken together are methylenedioxy ($-OCH_2O-$) and $R_6$ is hydrogen, $(C_1-C_6)$alkyl, $(C_3-C_6)$cycloalkyl, $(C_1-C_6)$alkoxy, nitro, hydroxy or halo;

each bond represented by ——— is individually present or absent;

X is $C(R_a)(R_b)$ or $NR_c$;

Y is $C(R_d)(R_e)$ or $NR_f$;

if present, $R_a$ and $R_b$ are each independently hydrogen or $(C_1-C_6)$alkyl if the bond between the 11- and 12-positions represented by ——— is absent; or $R_a$ is hydrogen or $(C_1-C_6)$alkyl and $R_b$ is absent if the bond between the 11- and 12-positions represented by ——— is present;

if present, $R_c$ and $R_f$ are each independently hydrogen or $(C_1-C_6)$alkyl if the bond between the 11- and 12-positions represented by ——— is absent; or $R_c$ and $R_f$ are each independently $(C_1-C_6)$alkyl or absent if the bond between the 11- and 12-positions represented by ——— is present; and if present, $R_d$ and $R_e$ are each independently hydrogen or $(C_1-C_6)$alkyl if the bond between the 11- and 12-positions represented by ——— is absent; or $R_d$ is hydrogen or $(C_1-C_6)$alkyl and $R_e$ is absent if the bond between the 11- and 12-positions represented by ——— is present;

provided that $R_2$ and $R_8$ are not both $(C_1-C_6)$alkoxy; and provided that $R_1-R_3$ and $R_6-R_8$ are not all hydrogen;

or a pharmaceutically acceptable salt thereof.

Another preferred compound of formula (I) is a compounds of formula (V):

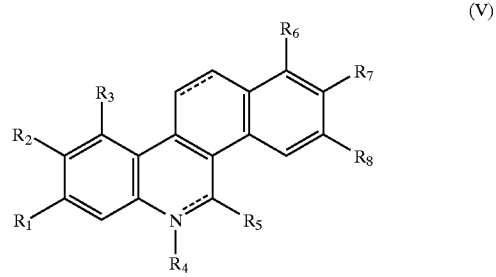

(V)

wherein $R_1-R_8$ are defined as hereinabove for the corresponding radical in a compound of formula I; each bond represented by ——— is individually present or absent; or a pharmaceutically acceptable salt thereof.

A preferred compound of the invention is 2,3-methylenedioxy-8,9-dimethoxybenzo[i]phenanthridine; or a pharmaceutically acceptable salt thereof.

A compound of formula I can be prepared by reducing the nitro group of a compound of formula II:

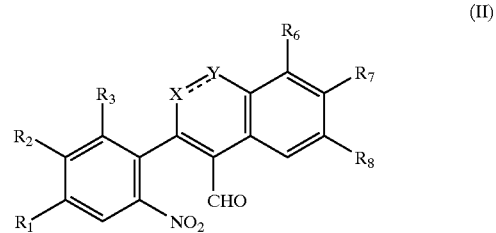

(II)

wherein $R_1-R_3$, $R_6-R_8$, X and Y are defined as they are for a compound of formula I, under conditions which give the imine ring closure product. Conditions suitable for reduction of the nitro group are well known to the art. For example, the hydrolysis may conveniently be carried out with zinc in acetic acid, under conditions similar to those described in Example 1.

Figure 2:
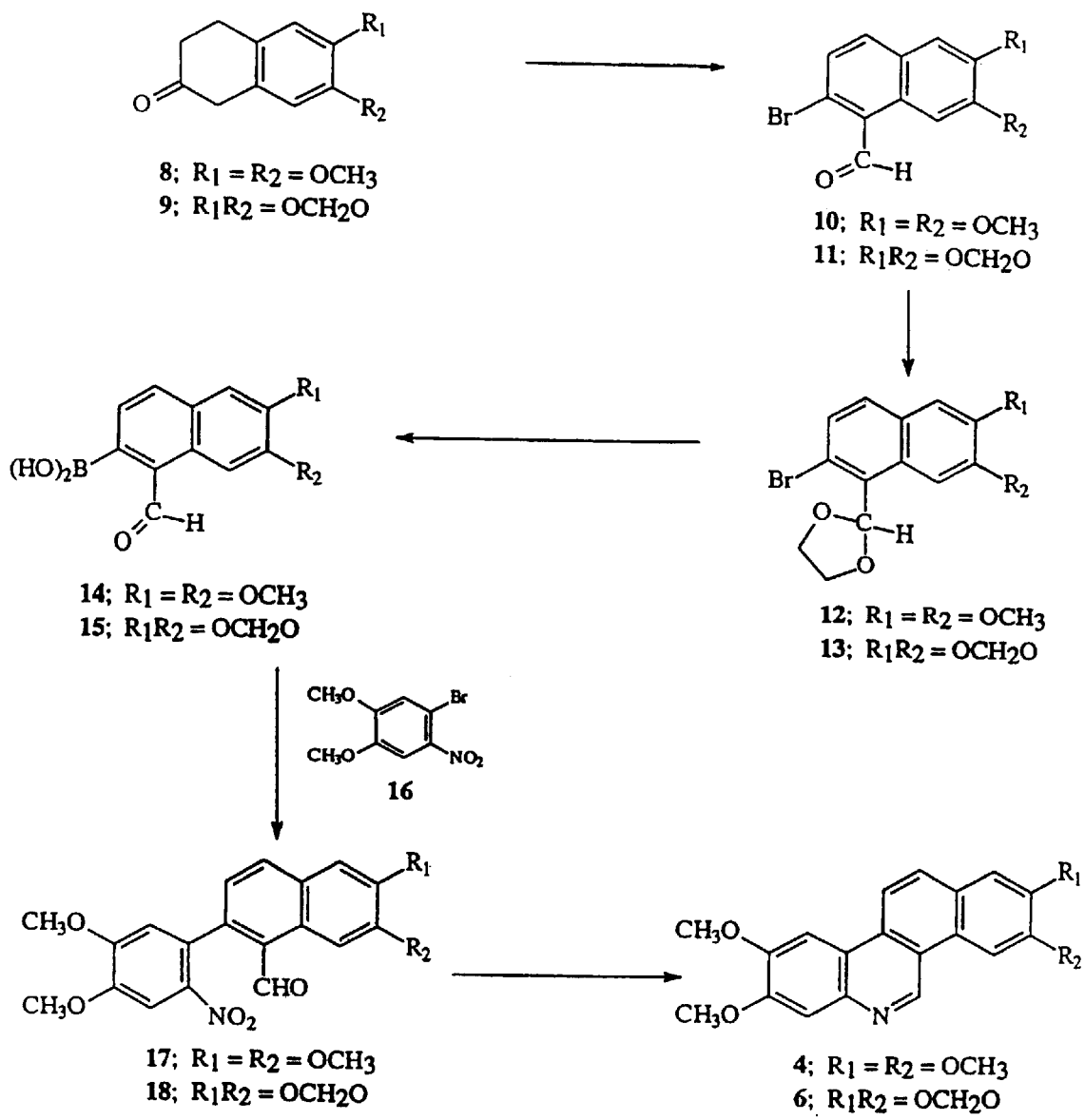
FIG. 2 Illustrates the synthesis of compounds of the invention.

An intermediate useful for preparing a compound of formula I, is a compound of formula II. A compound of formula II (for example compound 17 or 18) can be prepared using procedures similar to those illustrated in FIG. 2 and described in the sub-parts of Examples 1 and 3. Treatment of 6,7-dimethoxy-β-tetralone (8) and 6,7-methylenedioxy-β-tetralone (9) with dimethyl formamide and phosphorus tribromide gave the respective 3,4-dihydro-2-bromonapthaldehyde derivatives in about 70% yield, which were oxidized using DDQ in toluene quantitatively to the respective bromonapthaldehydes, 10 and 11. Acetals 12 and 13 were obtained in 95% yield by treatment of the respective bromonaphthaldehydes with ethylene glycol in presence of a catalytic amount of p-toluenesulfonic acid. A Dean-Stark apparatus was used to remove the water generated during the reaction. Lithium-halogen exchange was performed by treatment of the acetals 12 and 13 with butyllithium and then quenched with trimethylborate. Acidic work-up of the reaction products resulted in the formation of the boronic acid derivatives, 14 and 15 respectively. Palladium (0) catalyzed coupling of compounds 14 and 15 with the o-bromonitrobenzene derivative, 16, resulted in the formation of the 2-phenylnapthalene derivatives, 17 and 18, respectively, in about 80% yield. Reduction and concomitant cyclization of the nitro groups of 17 and 18 resulted in the of the desired benzo[i]phenanthridines, 4 and 6, respectively, in about 70% yield.

Figure 3:
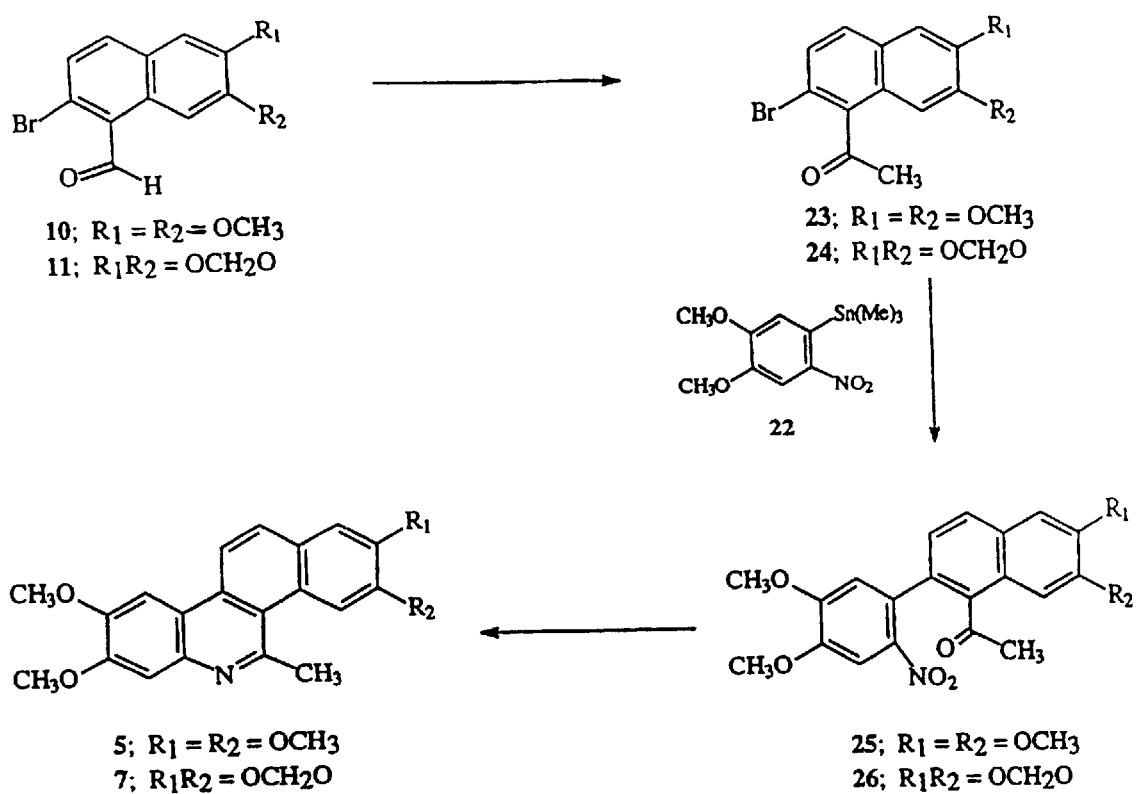
FIG. 3 Illustrates the synthesis of compounds of the invention.

A compound of formula II (for example compound 25 or 26) can also be prepared using procedures similar to those illustrated in FIG. 3 and described in the sub-parts of Examples 2 and 4. Grignard reactions performed on the respective naphthaldehydes, 10 and 11, with methylmagnesium bromide, followed by oxidation of the alcohols obtained with pyridinium chlorochromate resulted in the formation of the ketones 23 and 24, respectively. These ketones were then directly coupled with the tin compound (22) to give the 2-phenylnapthalenes 25 and 26, respectively. Reduction and concomitant cyclization of 25 and 26 occurred on treatment with zinc in acetic acid to give the desired 5-methyl substituted benzo[i]phenanthridines 5 and 7, respectively.

Figure 4:
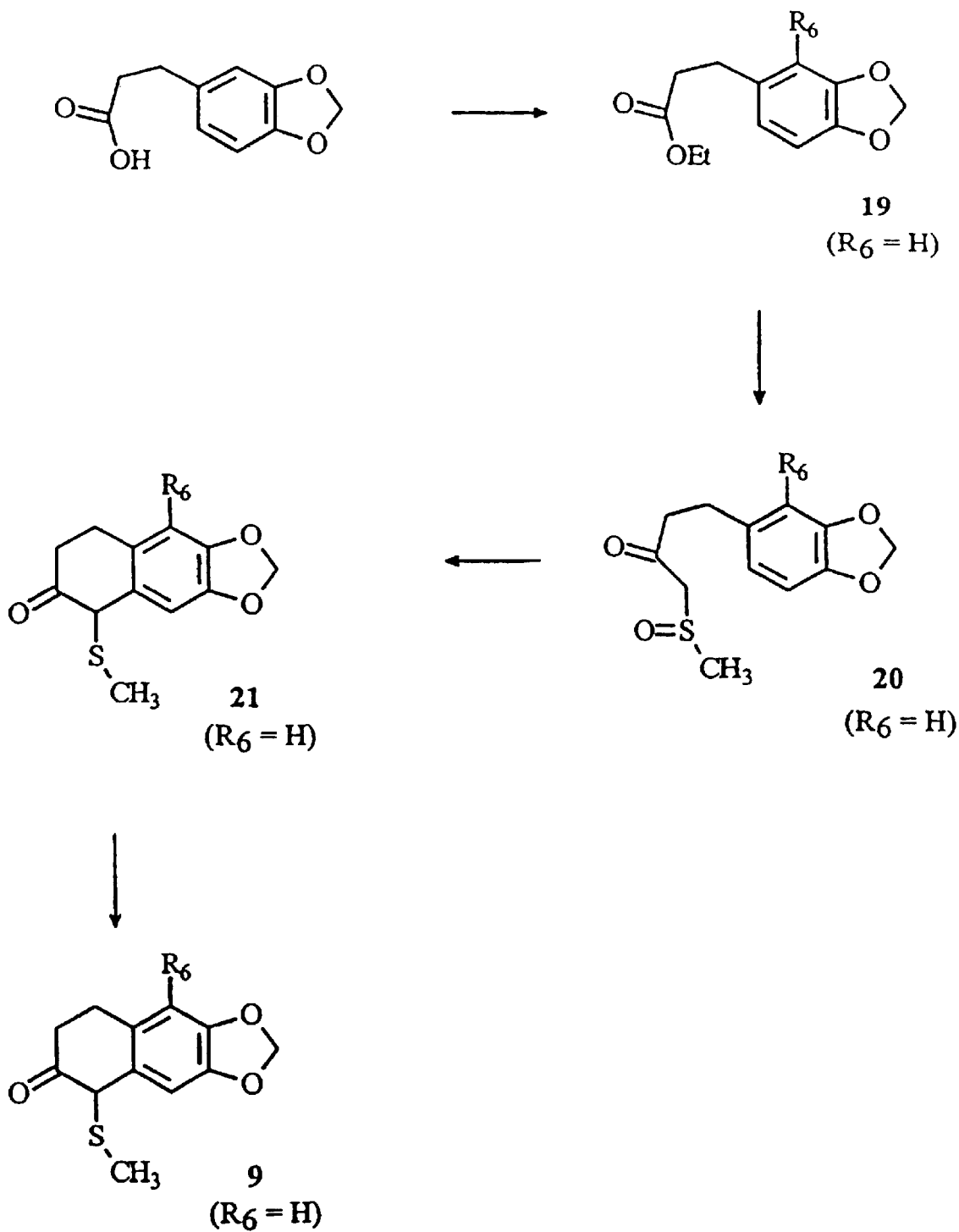
FIG. 4 Illustrates the synthesis of intermediate compound 9.

Another intermediate useful for preparing compounds of the invention is the β-tetralone 9, which can be prepared as illustrated in FIG. 4. 3,4-methylenedioxy-phenylpropionic acid was esterified to give ethyl ester, 19. Treatment of 19 with the anion of dimethyl sulfate resulted in the formation of the β-ketosulfoxide, 20, which cyclized on treatment with trifluoroacetic acid to the 1-methylthio-β-tetralone, 21. Reductive desulfurization of 21 gave 6,7-methylenedioxy-β-tetralone, 9.

Figure 5:
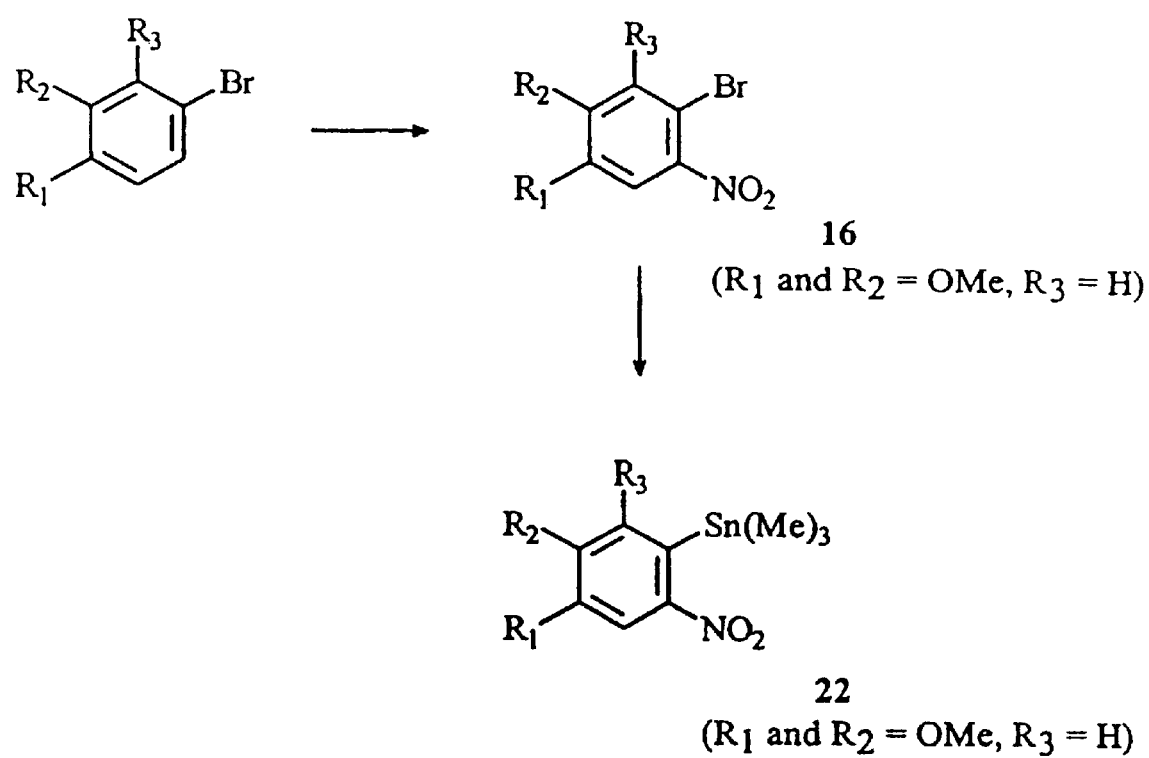
FIG. 5 Illustrates the synthesis of intermediate compound 22.

Another intermediate useful for preparing compounds of the invention is the compound 22, which can be prepared as illustrated in FIG. 5. Nitration of 4-bromo-1,2-dimethoxybenzene gave compound 16, which was treated with hexamethylditin to give the tin compound 22.

Figure 6:
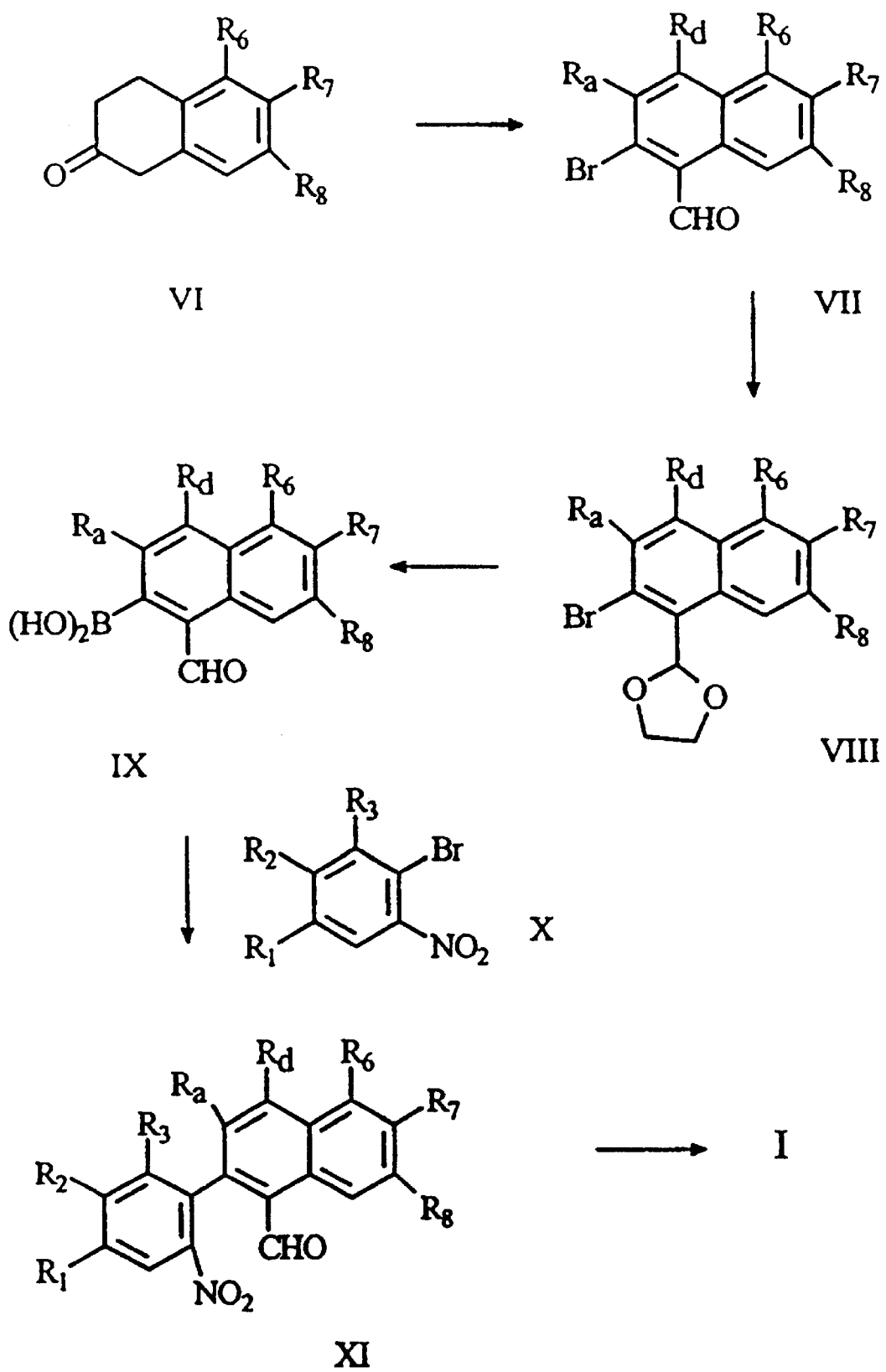
FIG. 6 Illustrates the synthesis of compounds of the invention wherein X is $CR_a$ and Y is $CR_d$.

As illustrated in FIG. 6, a compound of formula (I) wherein X is $CR_a$ and Y is $CR_d$ can be prepared using procedures similar to those described herein.

Figure 7:
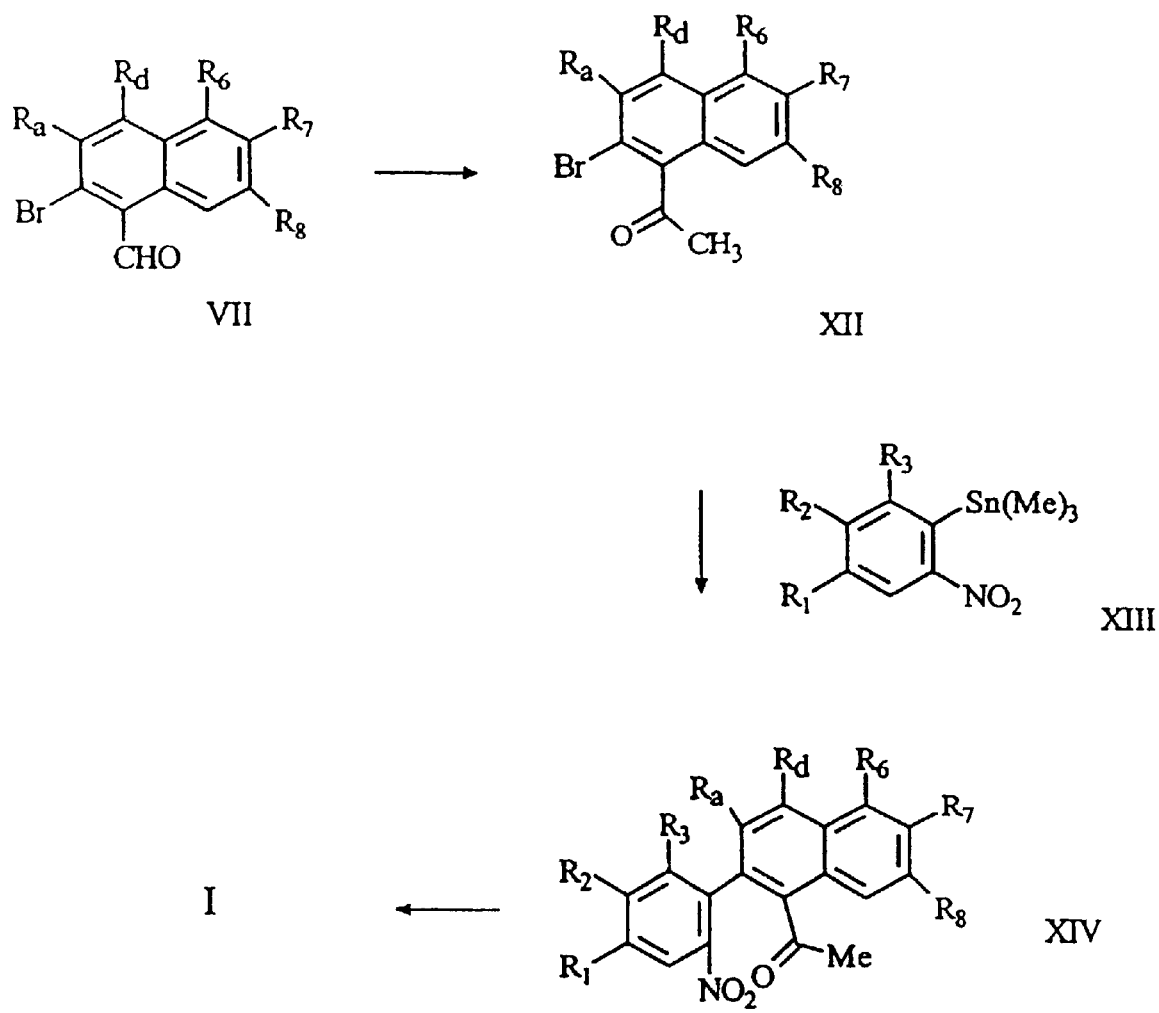
FIG. 7 Illustrates the synthesis of compounds of the invention wherein X is $CR_a$, Y is $CR_d$, and $R_5$ is alkyl.

As illustrated in FIG. 7, a compound of formula (I) wherein X is $CR_a$, Y is $CR_d$, and $R_5$ is alkyl can be prepared using procedures similar to those described herein.

A compound of formula (I) wherein X and/or Y is nitrogen can be prepared using techniques similar to those described by: M. J. S. Dewar and W. H. Poesche, A New Route to Polycyclic Benzocinnolines, *J. Chem. Soc.*, 2201–2203, 1963; R. S. W. Braithwaite and G. K. Robinson, Unsymmetrical Polynuclear Cinnoline Derivatives. Part I. Cyclisation of Some Cyclohexane-1,2-dione 1-Arylhydrazones, *J. Chem. Soc.*, 3671–3676, 1962; J. F. Corbett abd P. F. Holt, Polycyclic Cinnoline Derivatives. Part Viii. Cinnolines and their N-oxides and oo'-Diaminobiaryls, *J. Chem. Soc.*, 3695–3699, 1961.

The formation of quaternary N-methylated analogs of benzo[i]phenathridines can be accomplished by heating the compound neat in the presence of dimethyl sulfate in a sealed tube as described by A. R. Surrey, Org. Syn., Coll. Vol., 3, 753–756, 1955 in the preparation of Pyrocyanine, see below.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and αglycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure is form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound may conveniently be administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to effect topoisomerase I or II mediated DNA cleavage can be determined using pharmacological models that are well known to the art, for example, using a model like Test A described below.

Test A

Topoisomerase I and Topoisomerase II Cleavage Assay

Representative compounds of the invention were evaluated in cleavage assays for the recombinant topoisomerases I and calf thymus topoisomerases I and II. These assays were preformed as described by B. Gatto et al. *Cancer Res.*, 1996, 56, 2795–2800. Human topoisomerase I was isolated as a recombinant fusion protein using a T7 expression system. DNA topoisomerase II was purified from calf thymus gland as reported by Halligan, B. D.; Edwards, K. A.; Liu, L. F. "Purification and characterization of a type II DNA topoisomerase from bovine calf thymus," *J. Biol. Chem.* 1985, 260, 2475. Plasmid YEpG was purified by the alkali lysis method followed by phenol deproteination and CsCl/ethidium isopycnic centrifugation as described by Maniatis, T.; Fritsch, E. F.; Sambrook, *J. Molecular Cloning, a Laboratory Manual*; Cold Spring Harbor Laboratory: Cold Spring Harbor, N.Y. 1982; pp 149–185. The end-labeling of the plasmid was accomplished by digestion with a restriction enzyme followed by end-filling with Klenow polymerase as previously described by Liu, L. F.; Rowe, T. C.; Yang, L.; Tewey, K. M.; Chen, G. L. "Cleavage of DNA by mammalian topoisomerase II," *J. Biol. Chem.* 1983, 258, 15365.

The cytotoxic effects of a compound of the invention can be determined using pharmacological models that are well known to the art, for example, using a model like Test B described below.

Test B

Cytotoxicity Assay

The cytotoxicity was determined using the MTT-microtiter plate tetrazolinium cytotoxicity assay (MTA) (See Chen A. Y. et al. *Cancer Res.* 1993, 53, 1332; Mosmann, T. J., *J. Immunol. Methods* 1983, 65, 55; and Carmichael, J. et al. *Cancer Res.* 1987, 47, 936). The human lymphoblast RPMI 8402 and its camptothecin-resistant variant cell line, CPT-K5 were provided by Dr. Toshiwo Andoh (Aichi Cancer Center Research Institute, Nagoya, Japan) (see Andoh, T.; Okada, K. "Drug resistance mechanisms of topoisomerase I drugs," *Adv. in Pharmacology* 1994, 29B, 93. The cytotoxicity assay was performed using 96-well microtiter plates. Cells were grown in suspension at 37° C. in 5% $CO_2$ and maintained by regular passage in RPMI medium supplemented with 10% heat-inactivated fetal bovine serum, L-glutamine (2 mM), penicillin (100 U/mL), and streptomycin (0.1 mg/mL). For determination of $IC_{50}$, cells were exposed continuously with varying concentrations of drug and MTT assays were performed at the end of the fourth day.

TABLE 1

Pharmacological Activity of Compounds of the Invention

| Compound | Topo I-mediated DNA cleavage[b] | Topo II-mediated DNA cleavage[c] | Cytotoxicity $IC_{50}$[a] ($\mu$M) Cell Lines | |
| --- | --- | --- | --- | --- |
| | | | RPMI | CPT-K5 |
| 4 | >1000 | >1000 | 22.9 | 22.9 |
| 5 | >1000 | >1000 | 27.5 | >27.5[d] |
| 6 | 100 | 10 | 7.5 | 7.0 |
| 7 | 200 | 100 | 10.1 | 14.4 |
| 27 | 25 | >1000 | 1.3 | 5.2 |
| 28 | 25 | >1000 | 0.2 | 0.2 |
| 29 | 100 | >1000 | 15 | 20 |
| 30 | 250 | >1000 | 7.5 | 7.5 |
| 31 | 50 | >1000 | 3.0 | 3.0 |
| Nitidine | 1 | 1 | 0.65 | >2.6[d] |
| CPT | 1 | >1000 | 0.004 | >10[d] |
| VM-26 | >1000 | 1 | 0.3 | 0.5 |

[a]$IC_{50}$ has been calculated after 4 days of continuous drug exposure.
[b]Topoisomerase I cleavage values are reported as REC, Relative Effective Concentration, i.e., concentrations relative to camptothecin (CPT), whose value is arbitrarily assumed as 1, that are able to produce the same cleavage on the plasmid DNA in the presence of human topoisomerase I.
[c]Topoisomerase II cleavage values are reported as REC, Relative Effective Concentration, i.e., concentrations relative to VM-26, whose value is arbitrarily assumed as 1, that are able to produce the same cleavage on the plasmid DNA in the presence of calf thymus topoisomerase II. VM-26 (teniposide or epipodophyllotoxin) was obtained from the National Cancer Institute.
[d]$IC_{50}$ value substantially greater than the highest doses assayed Certain compounds of formula I, are potent topoisomerase I poisons. Additionally, compounds of formula I generally possess cytotoxic activity against RPMI 8402 cancer cells and camptothecin resistant CPT-K5 cells. Accordingly, compounds of formula I may be useful as cytotoxic agents, for the treatment of cancers, in particular, solid mammalian tumors or hematologic malignancies. Additionally, compounds of the invention may be useful as pharmacological tools for the further investigation of topoisomerase function.

As used herein, the term "solid mammalian tumors" include cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin central nervous system; sarcomas of the soft tissue and bone; and melanoma of cutaneous and intraocular origin. The term "hematological malignancies" includes childhood leukemia and lymphomas, Hodgkin's disease, lymphomas of lymphocytic and cutaneous origin, acute and chronic leukemia, plasma cell neoplasm and cancers associated with AIDS. The preferred mammalian species for treatment are humans and domesticated animals.

Compounds 6 and 7 exhibit potent activity as topoisomerase I poisons. This is believed to be due in part to the favorable placement of the methylenedioxy group. Compounds 4 and 5 demonstrate significantly less topoisomerase I poisioning activity. This is believed to be due to the presence of methoxy group at the ($R_8$) 3-position. Based on this reasoning, it might be expected that compound 28 would also possess diminished topoisomerase I poisioning activity, in view of the fact that there is a methoxy group at the 3-position. Compound 28, however, demonstrates potent topoisomerase poisioning activity.

This apparent anomaly can be explained by the fact that, if compound 28 (as shown in FIG. 1) is flipped vertically by 180 degrees, and then flipped horizontally by 180 degrees, it provides the following structure.

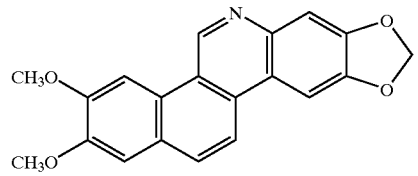

This structure has a methylenedioxy substituent in the positions corresponding to $R_7$ and $R_8$ in a compound of formula I. This suggests that benzo[i]phenanthridines having alkoxy substituents at either the 3- or 9-position should retain good topoisomerase poisioning activity, whereas those compounds having alkoxy substituents at both the 3- and 9-position may possess diminished activity. This also suggests that compounds having a nitrogen in the 12-position should retain topoisomerase poisioning activity.

The invention will now be illustrated by the following non-limiting Examples, wherein unless otherwise stated: melting points were determined with a Thomas-Hoover Unimelt capillary melting point apparatus; column chromatography refers to, flash chromatography conducted on Sil-iTech 32–63 $\mu$m, (ICN Biomedicals, Eschwegge, Ger.) using the solvent systems indicated; infrared spectral data (IR) were obtained on a Perkin-Elmer 1600 Fourier transform spectrophotometer and are reported in $cm^{-1}$; proton ($^1$H NMR) and carbon ($^{13}$C NMR) nuclear magnetic resonance were recorded on a Varian Gemini-200 Fourier Transform spectrometer; NMR spectra (200 MHz $^1$H and 50 MHz $^{13}$C) were recorded in the deuterated solvent indicated with chemical shifts reported in $\delta$ units downfield from tetramethylsilane (TMS); coupling constants are reported in hertz (Hz); mass spectra were obtained from Washington University Resource for Biomedical and Bio-organic Mass Spectrometry within the Department of Chemistry at Washington University, St. Louis, Mo.; and combustion analyses were performed by Atlantic Microlabs, Inc., Norcross, Ga., and were within ±0.4% of the theoretical value.

EXAMPLES

Example 1

2,3,8,9-Tetramethoxybenzo[i]phenanthridine (4)

Compound 17 (100 mg, 0.52 mmol) was dissolved in glacial acetic acid (8 mL) and heated to reflux with zinc dust (200 mg, 3.2 mmol) for 4 hours. The acetic acid was evaporated in vacuo, and the residue was extracted with chloroform. The chloroform solution was filtered through a celite bed. The filtrate was washed successively with saturated sodium bicarbonate solution and brine and evaporated to dryness. The residue was purified by chromatography (silica), with hexanes:ethyl acetate (1:1) as the eluent to give the title compound in 54% yield; mp=267–268° C.; IR (Nujol) 1621, 1513, 1982; $^1$H NMR $\delta$4.04 (3H, s), 4.06 (3H, s), 4.10 (3H, s), 4.13 (3H, s), 7.22 (1H, s), 7.55 (1H, s), 7.74 (1H, s), 7.89 (1H, d, J=8.8), 8.05 (1H, s), 8.18 (1H, d, J=8.8), 9.82 (1H, s); $^{13}$C NMR $\delta$56.4, 56.6, 102.0, 102.3, 108.5, 109.9, 118.3, 118.4, 120.7, 120.8, 125.7, 127.5, 130.7, 141.5, 145.9, 150.0, 150.1, 150.9, 151.4; HRMS calcd for $C_{21}H_{19}NO_4$: 349.1314; found: 349.1321.

The intermediate compound 17 was prepared as follows.

a. 2-Bromo-6,7-dimethoxy-1-napthaldehyde (10)

Dimethylformamide (3.0 g, 41 mmol) was added dropwise to solution of phosphorus tribromide (3.3 mL, 35 mmol) in dry chloroform (50 mL) at 0° C. The mixture was stirred at 0° C. for 1 h to give pale yellow suspension. A solution of compound 8 (2.0 g, 9.7 mmol) in chloroform was added to the yellow suspension and the mixture was heated at reflux for 1 h. The reaction mixture was cooled to 0° C. and saturated aqueous NaHCO$_3$ solution was added dropwise until no effervescence was obtained. The resulting mixture was extracted with dichloromethane, dried (Na$_2$SO$_4$) and evaporated to provide the respective 2-bromo-3,4-dihydro-1-napthaldehyde derivatives as yellow solids. Each of the 2-bromo-3,4-dihydro-1-naphthaldehyde derivatives were chromatographed on silica gel using a 3:1 mixture of hexanes:ethyl acetate as the eluent to give the 2-bromo-3,4-dihydro-1-naphthaldehydes in an 87% yield. The 2-bromo-3,4-dihydro-1-naphthaldehyde (2.4 g, 8.1 mmol) and DDQ (2.2 g, 97 mmol) was refluxed in toluene (50 mL) for 15 h. After cooling to room temperature, the mixture was subjected to filtration through a celite bed and the filtrate was evaporated to dryness. The residue obtained was chromatographed on 75 g silica gel using a 3:1 mixture of hexanes: ethyl acetate as eluent to give the 2-bromo-1-napthaldehyde in a 95% yield; $^1$H NMR $\delta$4.00 (3H, s), 4.05 (3H, s), 7.07 (1H, s), 7.54 (1H, d, J=8.5), 7.79 (1H, d, J=8.5), 8.71 (1H, s), 10.74 (1H, s); $^{13}$C NMR $\delta$56.3, 56.6, 104.2, 107.0, 126.5, 128.8, 129.4, 129.8, 129.9, 134.3, 150.4, 153.1, 195.9; HRMS calcd for $C_{13}H_{11}O_3Br$: 293.9891; found: 293.9896.

b. 2-Bromo-6,7-dimethoxynapthaldehyde-1-ethylacetal (12)

Compound 10 (540 mg, 1.95 mmol), ethylene glycol (0.7 mL) and p-toluenesulfonic acid (10 mg) were dissolved in 30 mL dry toluene. This reaction mixture refluxed under nitrogen in a flask fitted with a Dean-Stark apparatus to remove the water formed during acetal formation. At the end of the reaction (15 h), the solvent from the cooled reaction mixture was evaporated in vacuo and the residue obtained was dissolved in 50 mL ethyl acetate. The ethyl acetate solution was washed with a saturated solution of sodium bicarbonate, dried and the solvent was removed to give the crude acetal. Chromatography on silica gel using a 3:17 mixture of ethyl acetate:hexanes afforded the pure acetal as a clear viscous liquid in a 95% yield; IR (Nujol) 1660, 1635; $^1$H NMR $\delta$4.02 (3H, s), 4.06 (3H, s), 4.13–4.19 (2H, m), 4.38–4.48(2H, m), 7.09 (1H, s), 7.54–7.68 (2H, m), 7.72 (1H, s), 7.78 (1H, s); $^{13}$C NMR $\delta$56.2, 56.6, 65.7, 102.8, 104.6, 106.5, 122.9, 128.4, 129.1, 130.5, 131.2, 131.3, 148.0, 148.5; Anal. calcd for $C_{15}H_{15}O_4Br$: C, 53.11; H, 4.48; Found: C, 52.93; H, 4.51.

c. 1-Formyl-6,7-dimethoxynaphth-2-yl boronic acid (14)

Acetal 12 (1.4 mmol) was dissolved in 10 mL anhydrous tetrahydrofuran. This solution was stirred under nitrogen at –78 ° C. A hexanes solution of n-butyllithium (1.2 mL, 2.8 mmol) was added slowly and the reaction mixture was stirred at –78 ° C. for 30 min. A pale yellowish brown solution was obtained. To this yellow reaction mixture trimethylborate (0.5 mL, 4.2 mmol) was added and the resulting mixture was stirred at –78 ° C. for 1 h prior to allowing it to come to room temperature. A 5% solution of hydrochloric acid (20 mL) was added to the reaction mixture and stirred for 30 min at room temperature. The tetrahydrofuran was evaporated in vacuo and the water layer was extracted with dichloromethane. The combined organic layer was washed once with brine, dried and evaporated to give the boronic acid derivative 14, which was used in the subsequent step without further purification.

d. 2-(3,4-Dimethoxy-6-nitrophenyl)-6,7-dimethoxy-1-naphthaldehyde (17)

In a 3 neck flask compound 16 (876 mg, 3.34 mmol, prepared in sub-part e below) was taken with 430 mg of tetrakis(triphenylphosphine)palladium (0) in 20 mL dimethoxyethane and the resulting solution was stirred at room temperature under nitrogen for 30 min. The solution changed color from brown to yellow. A solution of compound 14 (1.1 mmol) in 5 mL dimethoxyethane was added to the reaction mixture followed by the addition of 5 mL of 2 M sodium carbonate solution. The reaction mixture was refluxed for 18 h. The reaction mixture was allowed to come to room temperature and the reaction mixture was filtered through a celite bed. The filtrate was evaporated to dryness and the residue obtained was column chromatographed on 75 g silica gel using 1:9 mixture of ethyl acetate:hexanes. The fourth compound eluting from the column was collected and the combined fractions were evaporated in vacuo to give the 2-phenyl-1-napthaldehyde derivative 17 in 22% yield, based on the acetal; mp=228–230; IR (Nujol) 1676, 1513, 1259. This compound was used for the synthesis of compound 4 without further characterization.

The intermediate compound 16 used in Example 1, sub-part d, was prepared as follows.

e. 3,4-Dimethoxy-6-nitro-bromobenzene (16)

3,4-Dimethoxybromobenzene (5 g, 23 mmol) was slowly added to a stirred solution of 35 mL concentrated nitric acid and 105 mL glacial acetic acid maintained at 10° C. The reaction mixture was stirred at 15° C. for 1 h and then diluted with 200 mL ice cold water. The resulting mixture was extracted thrice with 200 mL portions of ether. The combined organic phase was dried and evaporated in vacuo. The crude product was recrystallized from ethanol to give bright yellow needle shaped crystals of compound 16 in 92% yield; mp=122–124 ° C.; IR (Nujol) 1510, 1312; $^1$H NMR $\delta$3.94 (3H, s), 3.97 (3H, s), 7.12 (1H, s), 7.57 (1H, s); $^{13}$C NMR $\delta$56.9, 57.2, 108.0, 109.5, 117.0, 148.7, 153.3; Anal. calcd for $C_8H_8NO_4Br$: C, 36.72; H, 3.14; N, 5.30; Found: C, 36.70; H, 3.13; N, 5.29.

Example 2

5-Methyl-2,3,8,9-tetramethoxybenzo[i]phenanthridine (5)

Using a procedure similar to that described in Example 1, except replacing the compound 17 used therein with compound 25, the title compound was prepared in 60% yield; mp=255–257 °C.; IR (Nujol) 1620, 1513, 1209; $^1$H NMR δ3.42 (3H, s), 4.08 (6H, s), 4.13 (6H, s), 7.33 (1H, s), 7.52 (1H, s), 7.82 (1H, s), 7.98 (1H, d, J=8.8), 8.32 (1H, s), 8.35 (1H, d,J=8.8); $^{13}$C NMR δ31.6, 56.4, 56.5, 56.6, 102.1, 108.7, 108.8, 108.9, 118.6, 119.0, 122.2, 126.5, 129.0, 130.9, 132.6, 140.4, 149.1, 149.6, 149.7, 151.7, 154.9; HRMS calcd for $C_{22}H_{21}NO_4$: 363.1470; found: 363.1471.

The intermediate compound 25 was prepared as follows.

a. 1-Aceto-2-bromo-6,7-dimethoxynapthalene (23)

A 1.4 M solution of methylmagnesium bromide in tetrahydrofuran (16.8 mL, 16.8 mmol) was added to a solution of napthaldehyde 10 in 20 mL dry tetrahydrofuran at 0° C. under nitrogen. The reaction mixture was stirred for 1 h at 0° C. The reaction was quenched by dropwise addition of 100 mL water followed by rapid addition of 50 mL 0.1 N hydrochloric acid. The reaction mixture was extracted with ethyl acetate, dried and the solvent was evaporated in vacuo to give an oily residue. The oil was triturated with chloroform to give the alcohol as a white needle shaped crystalline solid in 95% yield. Pyridinium chlorochromate (857 mg, 3.98 mmol) was suspended in 10 mL dry dichloromethane. The alcohols (2.49 mmol) was added to this suspension and the resulting mixture was stirred under nitrogen at room temperature for 6 h. Ether (100 mL) was added to the reaction mixture and the suspension obtained was filtered through a celite bed. The filtrate was evaporated to dryness and the residue obtained was chromatographed on 75 g silica gel using a 1:9 mixture of ethyl acetate:hexanes to give the 1-aceto-2-bromonapthalene derivatives 23 as fluffy bright white needles in 85% yield; mp=102–103° C.; IR (Nujol) 1693; $^1$H NMR δ2.70 (3H, s), 3.95 (3H, s), 3.99 (3H, s), 6.84 (1H, s), 7.10 (1H, s), 7.43 (1H, d, J=8.4), 7.56 (1H, d, J=8.4); $^{13}$C NMR δ32.4, 56.4, 103.1, 107.2, 113.3, 126.3, 128.2, 128.7, 129.1, 139.0, 150.4, 151.4, 205.5; HRMS calcd for $C_{14}H_{13}O_3Br$: 308.0048; found: 308.0059.

b. 1-Aceto-2-(3,4-dimethoxy-6-nitrophenyl)-6,7-dimethoxynapthalene (25)

A mixture containing compound 22 (0.98 mmol), the 1-aceto-2-bromonapthalene 23 (0.89 mmol), $(Ph_3P)_4Pd$ (106 mg) and copper cyanide (17 mg) was refluxed in 20 mL toluene under nitrogen for 20–24 h. After cooling to room temperature, ethyl acetate (20 mL) was added to the reaction mixture and the organic layer was poured into a separating funnel. The organic layer was washed with 20 mL of distilled water. The two phases were allowed to separate as much as possible and the aqueous layer was discarded. The remaining emulsion was passed through a celite bed. The organic layer was separated from the filtrate and evaporated to dryness. The residue obtained was chromatographed on 75 g silica gel using a 3:2 mixture of hexanes:ethyl acetate to give the 1-aceto-2-(3,4-dimethoxy-6-nitrophenyl) naphthalene derivative 25 in 30% yield; mp=185–187° C.; IR (Nujol) 1689, 1503, 1260; $^1$H NMR δ2.25 (3H, s), 3.90 (3H, s), 3.98 (3H, s), 4.02 (3H, s), 4.03 (3H, s), 6.76 (1H, s) (1H, d, J=8.4), 7.12 (1H, s), 7.18 (1H, s), 7.70 (I H, s), 7.71 (1H, d, J=8.4); $^{13}$C NMR δ32.7, 56.4, 56.9, 57.0, 57.1, 103.8, 107.2, 108.5, 115.7, 124.9, 125.1, 128.2, 129.5, 130.1, 131.6, 136.9, 141.1, 149.0, 150.5, 151.2, 152.8, 208.0; HRMS calcd for $C_{21}H_{19}NO_7$—$C_2H_3O$: 368.1134; found: 368.1135.

The intermediate compound 22 used in sub-part b was prepared as follows.

c. 3,4-Dimethoxy-6-nitrophenyl-trimethylstannane (22)

A mixture of hexamethylditin (2.0 g, 6.1 mmol), compound 16 (1.56 g, 6.0 mmol) and $Pd(PPh_3)_4$ (163 mg, 0.14 mmol) in toluene (50 mL) was heated to reflux under nitrogen for 10 h. After cooling, 7 M KF aqueous solution (1 mL) was added with vigorous stirring. The mixture was passed though a celite bed and the filtrate was evaporated to dryness. The residue was chromatographed on 75 g silica gel using hexanes:ethyl acetate (5:1) as eluent. The relevant fractions were pooled and evaporated in vacuo to give 1.2 g of compound 22 in 58% yield; mp 115° C.; $^1$H NMR δ0.32 (9H, s), 3.94 (3H, s), 3.99 (3H, s), 7.03 (1H, s), 7.88 (1H, s); $^{13}$C NMR δ−7.2, 56.7, 107.7, 117.3, 134.0, 146.8, 149.8, 154.1; HRMS calcd for $C_{11}H_{17}NO_4Sn$—$CH_3$: 329.9937; found: 329.9939.

Example 3

2,3-Methylenedioxy-8,9-dimethoxybenzo[i] phenanthridine (6)

Using a procedure similar to that described in Example 1, except replacing the compound 17 used therein with compound 18, the title compound was prepared in 60% yield; mp>250° C.; IR (Nujol) 1680; UV ($CHCl_3$) 285, 360, 380 nm (log ε=3.01, 2.21, 2.47); $^1$H NMR δ4.10 (3H, s), 4.14 (3H, s), 6.15 (2H, s), 7.28 (1H, s), 7.68 (1H, s), 7.83 (1H, s), 7.97 (1H, d, J=9.2), 8.16 (1H, s), 8.28 (1H, d, J=9.2), 9.85 (1H, s); $^{13}$C NMR δ56.7, 100.3, 102.1, 102.2, 106.1, 109.2, 118.4, 127.5, 128.9, 131.2, 131.7, 140.8, 145.6, 145.7, 148.4, 149.9, 150.4, 151.7, 176.1; HRMS calcd for $C_{20}H_{15}NO_4$: 333.1001; found: 333.0999.

The intermediate compound 18 was prepared as follows.

a. Ethyl-3,4-(methylenedioxy)dihydrocinnamate (19)

Trimethylsilyl chloride 2.5 mL (18.2 mmol) was added to a solution of 1.5 g (7.7 mmol) of 3,4-(methylenedioxy) dihydrocinnamic acid in 70 mL dry ethanol and this mixture was stirred at room temperature under nitrogen for 12 h. The excess ethanol was evaporated in vacuo and the residue obtained was chromatographed on 100 g silica gel using 1:9 mixture respectively of ethyl acetate and hexanes to give a quantitative yield of the ester (19) as a colorless liquid; $^1$H NMR δ1.21 (3H, t), 2.60 (2H, t), 2.87 (2H, t), 4.08 (2H, q, J=14.1, 7.3), 5.90 (2H, s), 6.56–6.69 (3H, m); $^{13}$C NMR δ14.5, 25.1, 34.2,60.7, 100.8, 106.9, 121.8, 122.2, 122.5, 145.3, 147.1, 173.2; HRMS calcd for $C_{12}H_{14}O_4$: 222.0892; found: 222.0895.

b. 3,4-(Methylenedioxy)phenethylmethylsulfinylmethyl ketone (20)

The anion of dimethyl sulfoxide was prepared by adding 6.0 mL dry dimethyl sulfoxide to 600 mg sodium hydride and heating the mixture at 70–75° C. for 45 min under nitrogen. This reaction mixture was allowed to cool to room temperature and then transferred to a water bath maintained at 5–10° C. A solution of compound 19 (1.0 g, 4.54 mmol) in 6.0 mL dry dimethyl sulfoxide was added dropwise, over a period of 15 min, to the dimethyl sulfoxide anion generated previously. The reaction mixture was slowly allowed to come to room temperature and stirred for 2 h. The reaction mixture was poured into 100 mL cold water and acidified to pH 3–4 using 1.2 N hydrochloric acid and extracted five times with 40 mL portions of chloroform. The combined organic layer was washed twice with 100 mL portions of distilled water, dried over anhydrous sodium sulfate, filtered and evaporated in vacuo to give quantitative yield of 20 as a low melting buff colored solid. Compound 20 was found to be unstable to column chromatography using silica gel, however, $^1$H NMR of the crude compound indicated that it could be used for the synthesis of 21 without further purification; mp=60–62° C.; $^1$H NMR δ2.55 (3H, s), 2.75–2.82 (4H, m), 3.56–3.76 (2H, q, $J_1$=13.8, $J_2$=34.3), 5.82 (2H, s), (3H, m); $^{13}$C NMR δ29.3,41.4,47.4, 64.4, 101.3, 108.7, 109.3, 121.6, 134.4, 146.4, 148.1, 202.1.

c. 1,2,3,4-Tetrahydro-1-methylthio-6,7-methylenedioxy-2 (1H)-napthalenone (21)

Trifluoroacetic acid (0.3 mL, 3.7 mmol) was dissolved in 25 mL benzene and added to the reaction flask containing 470 mg (1.85 mmol) of compound 20. The reaction mixture was heated to reflux for 1.5 h. On cooling to room temperature the reaction mixture was transferred to a separating funnel and washed twice using 10 mL portions of a saturated solution of sodium bicarbonate. The benzene layer was dried over anhydrous sodium sulfate, filtered and evaporated in vacuo to give a red syrup which was chromatographed over 100 g of silica gel using 1:9 mixture respectively of ethyl acetate and hexanes to give 21 in 60% yield; mp=52° C.; $^1$H NMR δ2.05 (3H, s), 2.70–3.10 (4H, m), 4.02 (1H, s), 5.85 (1H, s) 6.65 (1H, d, J=8.1), 6.72 (1H, d, J=8.1); $^{13}$C NMR δ16.3, 21.1, 34.2, 54.1, 101.6, 107.9, 118.5, 123.0, 127.6, 145.1, 147.3, 203.5; HRMS calcd for $C_{12}H_{12}O_3S$: 236.0507; found: 236.0505.

d. 6,7-Methylenedioxy-2-tetralone (9)

A solution of 21 (669 mg, 2.83 mmol) in 10 mL glacial acetic acid was placed in a hydrogenation flask. To this mixture 460 mg of 10% Pd-C was added and the resulting mixture was shaken in a Parr apparatus at 40 psig of hydrogen for 40 h. The reaction mixture was filtered through a celite bed, which was washed thrice with 5 mL portions of glacial acetic acid. The glacial acetic acid was rotaevaporated to give the crude tetralone, 9. The crude tetralone was then treated with sodium bisulfite to convert it to the more stable bisulfite adduct. Pure tetralone was generated as required from its bisulfite adduct by treatment with 10% sodium carbonate solution followed by extraction with dichloromethane; mp=91–92° C. (lit[144]=88–91° C.); IR (Nujol) 1727; $^1$H NMR δ2.51 (2H, t), 2.97(2H, t), 3.48 (2H, s), 5.92 (2H, s), 6.58 (1H, s), 6.69 (1H, s); $^{13}$C NMR δ21.5, 37.7, 45.1, 101.4, 107.5, 118.5, 121.0, 127.8, 144.2, 146.4, 211.5; Anal. calcd for $C_{11}H_{10}O_3$: C, 69.46; H, 5.30; Found: C, 69.40; H, 5.29.

e. 2-Bromo-6,7-methylenedioxy-1-napthaldehyde (11)

Using a procedure similar to that described in Example 1, sub-part a, except replacing the compound 8 used therein with Compound 9, compound 11 was prepared in 96% yield; mp=165–166° C.; IR (Nujol) 1680; $^1$H NMR δ6.09 (2H, s), 7.05 (1H, s), 7.51 (1H, d, J=8.7), 7.63 (1H, d, J=8.7), 8.60 (1H, s), 10.68 (1H, s); $^{13}$C NMR δ102.1, 102.3, 104.6, 127.4, 129.5, 129.6, 130.1, 131.1, 134.6, 148.6, 151.7, 195.5; Anal. calcd for $C_{12}H_7O_3Br$: C, 51.60; H, 2.51; Found: C, 51.98; H, 2.48.

f. 2-Bromo-6,7-methylenedioxynapthaldehyde-1-ethylacetal (13)

Using a procedure similar to that described in Example 1, sub-part b, except replacing the compound 10 used therein with compound 11, compound 13 was prepared in 95% yield; IR (Nujol) 1665, 1617; $^1$H NMR δ4.11–4.18 (2H, m), 4.36–4.43 (2H, m), 6.03 (2H, s), 6.56 (1H, s), 7.05 (1H, s), 7.41–7.48 (2H, m), 7.73 (1H, s); $^{13}$C NMR δ65.6, 101.8, 102.6, 104.8, 106.3, 123.0, 128.0, 129.3, 130.4, 131.1, 131.5, 147.9, 148.6; Anal. calcd for $C_{14}H_{11}O_4Br$: C, 52.10; H, 3.41; Found: C, 52.52; H, 3.48.

g. 1-Formyl-6,7-methylenedioxynaphth-2-yl boronic acid (15)

Acetal 13 (1.4 mmol) was dissolved in 10 mL anhydrous tetrahydrofuran. This solution was stirred under nitrogen at −78° C. A hexanes solution of n-butyllithium (1.2 mL, 2.8 mmol) was added slowly and the reaction mixture was stirred at −78° C. for 30 min. A pale yellowish brown solution was obtained. To this yellow reaction mixture trimethylborate (0.5 mL, 4.2 mmol) was added and the resulting mixture was stirred at −78° C. for 1 h prior to allowing it to come to room temperature. A 5% solution of hydrochloric acid (20 mL) was added to the reaction mixture and stirred for 30 min at room temperature. The tetrahydrofuran was evaporated in vacuo and the water layer was extracted with dichloromethane. The combined organic layer was washed once with brine, dried and evaporated to give the boronic acid derivative 15, which was used in the subsequent step without further purification.

h. 2-(3,4-Dimethoxy-6-nitrophenyl)-6,7-methylenedioxy-1-naphthaldehyde (18)

Using a procedure similar to that described in Example 1, sub-part d, except replacing the compound 14 used therein with compound 15, compound 18 was prepared in 25% yield; mp=225° C.; IR (Nujol) 1670, 1515, 1309; $^1$H NMR δ3.92 (3H, s), 4.04 (3H, s), 6.13 (2H, s), 6.74 (1H, s), 7.13 (1H, d, J=8.3), 7.18 (1H, s), 7.77 (1H, s), 7.87 (1H, d, J=8.3), 8.76 (1H, s), 10.14 (1H, s); $^{13}$C NMR δ57.0, 57.1, 102.1, 103.1, 104.7, 108.2, 114.9, 125.7, 127.9, 128.8, 129.5, 131.5, 133.6, 141.2, 144.1, 148.6, 149.2, 151.6, 152.9, 193.6.

Example 4

8,9-Dimethoxy-5-methyl-2,3-methylenedioxybenzo[i]-phenanthridine (7)

Using a procedure similar to that described in Example 1, except replacing the compound 17 used therein with compound 26, the title compound was prepared in 63% yield; mp>250° C.; IR (Nujol) 1685; UV (CHCl$_3$) 280, 365, 385 nm (log ε=2.79, 1.90, 2.03); $^1$H NMR δ3.36 (3H, s), 4.08 (3H, s), 4.13 (3H, s), 6.15 (2H, s), 7.31 (1H, s), 7.51 (1H, s), 7.80 (1H, s), 7.93 (1H, d, J=9.1), 8.29–8.35 (2H, m); $^{13}$C NMR δ31.7, 56.6, 102.1, 105.8, 106.3, 108.8, 118.5, 119.1, 122.9, 127.9, 130.2, 131.3, 132.7, 137.1, 140.3, 147.3, 148.8, 149.7, 151.7, 155.2; HRMS calcd for $C_{21}H_{17}NO_4$: 347.1158; found: 347.1156.

The intermediate compound 26 was prepared as follows.

a. 1-Aceto-2-bromo-6,7-methylenedioxynapthalene (24)

Using a procedure similar to that described in Example 3, sub-part a, except replacing the compound 10 used therein with compound 11, compound 24 was prepared in 90% yield; mp=138° C.; IR (Nujol) 1695; $^1$H NMR δ2.67 (3H, s), 6.06 (2H, s), 6.89 (1 H, s), 7.09 (1H, s), 7.41 (1H, d, J=8.8), 7.56 (1H, d, J=8.8); $^{13}$C NMR δ32.4, 101.0, 102.1, 104.9, 113.6, 127.6, 128.4, 129.6, 130.1, 139.8, 148.6, 149.7, 205.2; HRMS calcd for $C_{13}H_9O_3Br$: 291.9735; found: 291.9730.

b. 1-Aceto-2-(3,4-dimethoxy-6-nitrophenyl)-6,7-methylenedioxy-napthalene (26)

Using a procedure similar to that described in Example 3, sub-part b, except replacing the compound 23 used therein with compound 24, compound 26 was prepared in 20% yield; mp=190–192° C.; IR (Nujol) 1680, 1523, 1300; $^1$H NMR δ2.23 (3H, s), 3.89 (3H, s), 4.01 (3H, s), 6.07 (2H, s), 6.75 (1H, s), 7.06 (1H, d, J=8.4), 7.10 (1H, s), 7.16 (1H, s), 7.66 (2H, m); $^{13}$C NMR δ32.6, 56.9, 57.1, 101.7, 102.6, 105.0, 108.4, 115.6, 125.1, 126.0, 128.7, 129.5, 130.8, 131.5, 133.8, 144.5, 149.6, 150.5, 150.7, 152.8, 207.6.

Example 5

2,3-Dimethoxy-9-benzyloxybenzo[i]phenanthridine (30)

2-(4-Benzyloxy-6-nitrophenyl)-6,7-dimethoxy-1-naphthaldehyde (100 mg, 0.23 mmol) was dissolved in glacial acetic acid (15 mL) and heated to reflux with zinc dust (163 mg, 2.5 mmol) for 3.5 h. Acetic acid was evaporated in vacuo and the residue was dissolved in chloroform. The solution was filtered through a celite bed and the filtrate was washed successively with saturated sodium bicarbonate solution and brine. The organic layer was dried over anhydrous sodium sulfate, filtered and evaporated in vacuo. The residue was chromatographed over 50 g of silica gel using 1:2 mixture respectively of hexanes and ethyl acetate to give the title compound as a white solid in 56% yield; $^1$H NMR(CDCl$_3$) δ4.08(3H, s), 4.18(3H, s), 5.29(2H, s), 7.33 (1H, s), 7.42(5H, m), 7.52(1H, d, J=8.9), 7.72(1H, d, J=2.6), 8.02(1H, d, J=8.9), 8.17(1H, s), 8.39(1H, d, J=8.9), 8.52(1H, d, J=8.9), 10.04(1H, s); $^{13}$C NMR(CDCl$_3$) δ56.5, 56.6,70.8, 102.3, 108.6, 110.9, 112.8, 118.4, 119.6, 120.7, 124.2, 125.8, 127.7, 128.2, 128.6, 129.2, 131.4, 131.7, 137.1, 146.8, 148.6, 150.1, 151.2, 159.5; HRMS calcd for C$_{26}$H$_{24}$N$_3$: 395.1521, found: 395.1522.

The intermediate nitroaldehyde was prepared as follows.

a. 2-Bromo-3,4-dihydro-6,7-dimethoxy-1-napthaldehyde

Dimethylformamide (1.6 ml, 20 mmol) was added dropwise to a solution of phosphorus tribromide (1.6 ml, 17 mmol) in dry chloroform (25 ml) at 0° C. The mixture was stirred at 0° C. for 1 h to give pale yellow suspension. A solution of 6,7-Dimethoxy-2-tetralone (1.0 g, 4.9 mmol) in dry chloroform(20 ml) was added to the yellow suspension and the mixture was heated at reflux for 1 h. The reaction mixture was cooled to 0° C. and saturated aqueous NaHCO, solution was added dropwise until no effervescence was obtained. The resulting mixture was extracted with dichloromethane, dried over anhydrous sodium sulfate, filtered and evaporated in vacuo. The residue was chromatographed over 100 g of silica gel using 3:1 mixture respectively of hexanes and ethyl acetate to give the bromoaldehyde in 80% yield; $^1$H NMR(CDCl$_3$) δ2.83(2H, t, J=8.0), 3.88(3H, s), 3.89(3H, s), 6.66(1H, s), 7.71(1H, s), 10.31(1H, s); $^{13}$C NMR(CDCl$_3$) δ28.9, 38.5, 56.4,56.5, 110.0, 111.1, 123.0, 128.0, 132.7, 144.2, 147.7, 149.1, 193.6.

b. 2-Bromo-6,7-dimethoxy-1-napthaldehyde

2-Bromo-3,4-dihydro-6,7-dimethoxy-1-napthaldehyde (960 mg, 3.23 mmol) and DDQ (880 mg, 3.88 mmol) was refluxed in toluene(45 mL) for 12 h. After cooling to room temperature, the mixture was subjected to filtration through a celite bed and the filtrate was evaporated to dryness. The residue obtained was chromatographed on 100 g silica gel using 3:1 mixture respectively of hexanes and ethyl acetate to give the aromatic compound in 95% yield; IR(KBr) 1671; $^1$H NMR(CDCl$_3$) δ4.00(3H, s), 4.05(3H, s), 7.07(1H, s), 7.54(1H, d, J=8.5), 7.79(1H, d, J=8.5), 8.71(1H, s) 10.74 (1H, s); $^{13}$C NMR(CDCl$_3$) δ56.3, 56.6, 104.2, 107.0, 126.5, 128.8, 129.4, 129.8, 129.9, 134.3, 150.4, 153.1, 195.9; HRMS calcd for C$_{13}$H$_{11}$O$_3$Br: 993.9891; found: 293.9896.

c. 4-Bromo-3-nitrophenol

4-Bromo-3-nitroanisole (2.32g, 10 mmol) was dissolved in 25 mL dichloromethane and cooled in an acetone-dry ice bath at −78° C. under nitrogen. A solution of BBr$_3$ (1.0M in dichloromethane) (25 mL, 25 mmol) was added dropwise. Gradually increased temperature to 20° C., stirred for 30 h. The reaction mixture was cooled to 0° C. and distilled water (30 mL) was added dropwise. The aqueous layer was extracted with ethyl acetate (30 mL×2). The combined organic layer was washed successively with saturated NaHCO, solution (30 mL×2). The organic layer was dried over anhydrous sodium sulfate, filtered and evaporated in vacuo. The residue was chromatographed over 100 g of silica gel using 3:1 mixture respectively of hexanes and ethyl acetate to give the phenol in 70% yield; $^1$H NMR (CDCl$_3$) δ6.92(1H, dd, J$_1$=2.9, J$_2$=8.8), 7.36(1H, d, J=2.9), 7.56(1H, d, J=8.8); $^{13}$C NMR(CDCl$_3$) δ105.2 113.4, 116.4, 121.4, 136.3, 155.9; HRMS calcd for C$_6$H$_4$NO$_3$Br: 216.9374, found: 216.9375.

d. 5-Benzyloxy-2-bromonitrobenzene

A solution of 4-Bromo-3-nitrophenol (1.0 g, 4.6 mmol) and benzyl bromide (0.82 mL, 7 mmol) in acetonitrile (30 mL) and acetone (15 mL) was treated with K$_2$CO$_3$ (970 mg, 7 mmol). The resulting mixture was heated at reflux under nitrogen for 17 h. The reaction mixture was evaporated in vacuo and the residue was dissolved in 40 mL ethyl acetate. The solution was filtered under vacuum then the filtrate was washed successively with distilled water (30 mL), 1M HCl solution (30 mL×3), brine (30 mL). The organic layer was dried over anhydrous sodium sulfate, filtered and evaporated in vacuo. The residue was chromatographed over 100 g of silica gel using 3:1 mixture respectively of hexanes and ethyl acetate to give the benzyl alcohol in 95% yield; $^1$H NMR(CDCl$_3$) δ5.11(2H, s), 7.02(1 H, dd, J$_1$=2.9, J$_2$=8.9), 7.41(5H, m), 7.46(1 H, d, J=2.9), 7.60(1H, d, J=8.9); $^{13}$C NMR(CDCl$_3$) δ71.4, 105.4, 112.4, 121.1, 128.1, 128.9, 129.1, 129.3, 129.5, 135.8, 136.0, 138.2, 158.7; HRMS calcd for C$_{13}$H$_{10}$NO$_3$Br: 306.9844; found: 306.9846.

e. 4-Benzyloxy-2-nitrophenyl-trimethylstannane

A mixture of hexmethylditin (1.0 g, 3 mmol), 5-Benzyloxy-2-bromonitrobenzene (462 mg, 1.5 mmol) and Pd(PPh$_3$), (70 mg) in anhydrous THF (25 ml) was heated to reflux under nitrogen for 18 h. After cooling to room temperature, THF was evaporated and methylene chloride (30 ml) was added to the residue. To this mixture, potassium fluoride solution (7M, 2 ml) was added dropwise with vigorous stirring. The mixture was passed through a celite bed and the filtrate was washed with brine. The methylene chloride layer was dried over anhydrous sodium sulfate, filtered and evaporated in vacuo. The residue was chromatographed over 100 g of silica gel using 6:1 mixture respectively of hexanes and ethyl acetate to give the stannane in 70% yield; $^1$H NMR(CDCl$_3$) δ0.32 (9H, s), 5.16(2H, s), 7.24(1H, dd, J$_1$=2.5, J$_2$=8.1), 7.42(5H, m), 7.56(1H, d, J=8.1), 7.95(1H, d, J=2.5); $^{13}$C NMR(CDCl$_3$) δ−7.3, 70.9, 110.4, 121.8, 128.0, 128.8, 129.2, 130.7, 136.4, 138.2. 154.6, 160.3.

f. 2-(4-Benzyloxy-6-nitrophenyl)-6,7-dimethoxy-1-naphthaldehyde

Pd(PPh$_3$)$_4$ (60 mg, 0.07 mmol) and CuBr (10 mg, 0.07 mmol) was added to a solution of compound 2-bromo-6,7-dimethoxy-1-napthaldehyde (204 mg, 0.69 mmol) and 4-benzyloxy-2-nitrophenyl-trimethylstannane (320 mg, 0.82 mmol) in THF(20 mL). The resulted mixture was refluxed under nitrogen for 6 h. After cooling to room temperature, THF was evaporated and ethyl acetate (30 mL) was added to the residue. The resulting solution was washed with distilled water (20 mL). The two phases was separated as much as possible and the aqueous layer was discarded. The remaining was passed through a celite bed. Seperated organic layer was washed with brine. The organic layer was dried over anhydrous sodium sulfate, filtered and evaporated in vacuo. The residue was chromatographed over 75 g of silica gel using 3:1 mixture respectively of hexanes and ethyl acetate to give the nitroaldehyde as light yellow solid in 92% yield; $^1$H NMR(CDCl$_3$) δ4.05(3H, s), 4.09(3H, s), 5.21(2H, s), 7.12(1H, d, J=8.3), 7.18(1H, s), 7.28(1H, d, J=2.3), 7.30(1H, s), 7.45(5H, m), 7.72(1H, d, J=2.3), 7.88 (1H, d, J=8.3), 8.86(1H, s), 10.18(1H, s); $^{13}$C NMR(CDCl$_3$) δ56.3, 56.6,71.4, 105.2, 107.1, 110.9, 114.1, 120.0, 123.9, 125.8, 126.4, 127.1, 127.4, 128.1, 129.0, 129.4, 130.3, 133.2, 134.7, 135.9, 150.3, 150.9, 168.8, 193.9; HRMS calcd for C$_{26}$H$_{21}$NO$_6$: 443.1369, found: 443.1370.

Example 6

2,3-Dimethoxy-9-aminobenzo[i]phenanthridine (31)

2-(4,6-Dinitrophenyl)-6,7-dimethoxy-1-naphthaldehyde (100 mg, 0.26 mmol) was dissolved in glacial acetic acid (15 mL) and heated to reflux with zinc dust (180 mg, 2.7 mmol) for 3 h. Acetic acid was evaporated in vacuo and the residue was dissolved in chloroform. The solution was filtered through a celite bed and the filtrate was washed successively with saturated sodium bicarbonate solution and brine. The organic layer was dried over anhydrous sodium sulfate, filtered and evaporated in vacuo. The residue was chromatographed over 50 g of silica gel using 8:1 mixture respectively of ethyl acetate and methanol to give the title compound as an orange-yellow solid in 30% yield; $^1$H NMR(CD$_3$OD) δ3.95(3H, s), 4.04(3H, s), 7.12(1H, dd, $J_1$=8.8, $J_2$=2.3), 7.22(1H, d, J=2.3), 7.26(1H, s), 7.86(1H, d, J=9.0), 7.98(1H, s), 8.17(1H, d, J=9.0), 8.29(1H, d, J=8.8), 9.68(1H, s); $^{13}$C NMR(CD$_3$OD) δ59.3, 59.5, 105.0, 112.4, 112.9, 120.9, 121.4, 122.6, 123.2, 127.7,129.7, 131.2, 135.7, 136.2, 149.5, 151.3, 153.5, 153.7, 155.1; HRMS calcd for C$_{19}$H$_{16}$N$_2$O$_2$: 304.1212, found: 304.1212.

The intermediate nitro aldehyde was prepared as follows.

a. 2,4-Dinitro-trimethylstannane

A mixture of hexmethylditin (1.0 g, 3.0 mmol), and 2,4-dinitroiodobenzene (588 mg, 2.0 mmol) and Pd(PPh$_3$)$_4$ (95 mg) in anhydrous THF (25 ml) was heated to reflux under nitrogen for 18 h. After cooling to room temperature, THF was evaporated and methylene chloride (30 ml) was added to the residue. To this mixture, potassium fluoride solution (7M, 2 ml) was added dropwise with vigorous stirring. The mixture was passed through a celite bed and the filtrate was washed with brine. The methylene chloride layer was dried over anhydrous sodium sulfate, filtered and evaporated in vacuo. The residue was chromatographed over 100 g of silica gel using 6:1 mixture respectively of hexanes and ethyl acetate to give the stannane as shining yellow crystals in 53% yield; $^1$H NMR(CDCl$_3$) δ0.43(9H, s), 7.93(1 H, d, J=8.0), 8.42(1H, dd, $J_1$=8.0, $J_2$=2.1), 9.11(1H, d, J=2.1); $^{13}$C NMR(CDCl$_3$) δ−6.9, 119.2, 127.2, 139.0, 149.4, 150.0, 154.1; HRMS calcd for CH$_9$N$_{12}$O$_4$Sn—CH: 316.9584; found: 316.9584.

b. 2-(4,6-Dinitrophenyl)-6,7-dimethoxy-1-naphthaldehyde

Pd(PPh$_3$)$_4$ (60 mg, 0.07 mmol) and CuBr (10 mg, 0.07 mmol) was added to a solution of compound 2-Bromo-6,7-dimethoxy-1-napthaldehyde (186 mg, 0.63 mmol) and compound 2,4-dinitrotrimethylstannane (250 mg, 0.76 mmol) in THF(20 mL). The resulted mixture was refluxed under nitrogen for 6 h. After cooling to room temperature, THF was evaporated and ethyl acetate (30 mL) was added to the residue. The resulting solution was washed with distilled water (20 mL). The two phases was seperated as much as possible and the aqueous layer was discarded. The remaining was passed through a celite bed. Seperated organic layer was washed with brine. The organic layer was dried over anhydrous sodium sulfate, filtered and evaporated in vacuo. The residue was chromatographed over 75 g of silica gel using 3:1 mixture respectively of hexanes and ethyl acetate to give the nitroaldehyde as yellow solid in 95% yield; $^1$H NMR(CDCl$_3$) δ4.06(3H, s), 4.10(3H, s), 7.10(1H, d, J=8.3), 7.22(1H, s), 7.64(1H, d, J=8.3), 7.95(1H, J=8.3), 8.50(1H, dd, $J_1$=8.3, $J_2$=2.3), 8.63(1H, s), 8.96(1H, d, J=2.3), 10.30 (1H, s); $^{13}$C NMR(CDCl$_3$) δ56.4, 56.7, 104.3, 107.1, 120.5, 124.5, 126.9, 128.0, 131.0, 133.4, 134.7, 139.3, 142.2, 148.0, 149.3, 151.0, 153.4, 191.9; HRMS calcd for C$_{19}$H$_{14}$N$_2$O$_7$: 382.0801, found: 382.0801.

Example 7

2,3,8,9-Dimethylenedioxybenzo[i]phenanthridine (29)

Compound 2-(3,4-methylenedioxy-6-nitophenyl)-6,7-methylenedioxy-1-naphthaldehyde (100 mg, 0.30 mmol) was dissolved in glacial acetic acid (20 mL) and heated to reflux with znic dust (200 mg, 3.2 mmol) for 3 h. Acetic acid was evaporated in vacuo and the residue was dissolved in chloroform. The solution was filtered through a celite bed and the filtrate was washed successively with saturated sodium bicarbonate solution and brine. The organic layer was dried over anhydrous sodium sulfate, filtered and evaporated in vacuo. The residue was chromatographed over 75 g of silica gel using 1:1 mixture respectively of hexanes and ethyl acetate to give the title compound in 40% yield; $^1$H NMR(CDCl$_3$) δ6.17(2H, s), 6.18(2H, s), 7.31(1H, s), 7.58 (1H, s), 7.92(1H, s), 7.96(1H, d, J=9.2), 8.20(1H, s), 8.25 (1H, d, J=9.2), 9.88(1H, s); $^{13}$C NMR(CDCl$_3$) δ99.8, 100.4, 102.1, 102.3, 106.2, 107.7, 118.8, 123.9, 127.0, 127.9, 130.9, 131.3, 146.2, 148.3, 149.7, 151.3, 152.0, 152.9, 154.7; HRMS calcd for C$_{19}$H$_{14}$NO$_4$: 317.0688, found: 317.0688.

The intermediate nitro aldehyde was prepared as follows.

a. 3-(3,4-Methylenedioxyphenyl) propionyl chloride 3-(3,4-Methylenedioxyphenyl) propionic acid (600 mg, 3.0 mmol) was suspended in methylene chloride (10 ml) and catalytic amount of pyridine (1 drop) was added. Thionyl chloride (0.27 ml, 3.6 mmol) was then added dropwise and the reaction mixture was stirred vigorously under nitrogen at room temperature for 20 h. After reaction was completed (monitored by TLC), reaction mixture was evaporated in vacuo to give a quantitative yield of the acid chloride as a yellow oil which was used without further purifications. $^1$H NMR(CDCl$_3$) δ2.93(2H, t, J=7.3), 3.16(2H, t, J=7.3), 5.94 (2H, s), 6.63(1H, d, J=7.7), 6.68(1H,s), 6.73(1H, d, J=7.7); $^{13}$C NMR(CDCl$_3$) δ31.3, 40.3, 101.5, 108.9, 109.2, 121.8, 132.8, 146.9 148.3 173.5.

b. 1-[2-(Diazomethylcarbonyl)ethyl]-3,4-methylenedioxybenzene

To a solution of TMSCHN$_2$ (3 ml, 6 mmol, 2M in hexane) in 5 ml THF-acetonitrile (1:1) was added dropwise a solution of compound 3-(3,4-Methylenedioxyphenyl)-propionyl chloride (600 mg, 3 mmol) in 5 ml THF-acetonitrile (1:1) at 0° C. The resulted mixture was stirred at 0° C. for 4 h. After reaction was completed, reaction mixture was evaporated in vacuo to give the diazo compound as a red viscous oil in 95% yield which was used without further purifications.

c. 6,7-Methylenedioxy-2-tetralone

To a solution of rhodium(II) acetate in dichloromethane (15 ml) was added dropwise a dichloromethane solution of compound 1-[2-(diazomethylcarbonyl)ethyl]-3,4-methylenedioxybenzene. The resulted mixture was refluxed under nitrogen for 1 h. Then the reaction mixture was evaporated in vacuo to give the tetralone as deep yellow crystals in 90% yield which was used without further purifications. mp=91–92° C.; IR(Nujol) 1727; $^1$H NMR (CDCl$_3$) δ2.52(2H, t, J=6.9), 2.96(2H, t, J=6.9), 3.48(2H, s),5.93(2H, s), 6.60(1H, s), 6.71(1H, s); $^{13}$C NMR(CDCl$_3$) δ28.7, 38.7, 45.4, 101.4, 108.7, 108.9, 121.7, 126.6, 130.3, 147.0, 210.9; Anal calcd for C$_{11}$H$_{16}$O$_3$: C, 69.46; H, 5.30; found: C, 69.40; H, 5.29.

d. 2-Bromo-3,4-dihydro-6,7-methylenedioxy-1-napthaldehyde

Dimethylformamide (0.8 ml, 10 mmol) was added dropwise to a solution of phosphorus tribromide (0.8 ml, 8.5 mmol) in dry chloroform (20 ml) at 0° C. The mixture was stirred at 0° C. for 1 h to give pale yellow suspension. A solution of compound 6,7-methylenedioxy-2-tetralone (500 mg, 2.6 mmol) in dry chloroform(20 ml) was added to the yellow suspension and the mixture was heated at reflux for 1 h. The reaction mixture was cooled to 0° C. and saturated aqueous NaHCO$_3$ solution was added dropwise until no effervescence was obtained. The resulting mixture was extracted with dichloromethane, dried over anhydrous sodium sulfate, filtered and evaporated in vacuo. The residue was chromatographed over 100 g of silica gel using 3:1 mixture respectively of hexanes and ethyl acetate to give the aldehyde in 60% yield; $^1$H NMR(CDCl$_3$) δ2.80(2H, t, J=7.8), 2.98(2H, t, J=7.8), 5.93(2H, s), 6.64(1H, s), 7.57(1H, s), 10.28(1H, s); $^{13}$C NMR(CDCl$_3$) δ29.3, 30.4, 101.6, 107.3,108.6, 124.0, 129.7, 132.7, 114.0, 146.7, 147.7, 193.2.

e. 2-Bromo-6,7-methylenedioxy-1-napthaldehyde

2-Bromo-3,4-dihydro-6,7-methylenedioxy-1-napthaldehyde (160 mg, 0.57 mmol) and DDQ (154 mg, 0.68 mmol) was refluxed in toluene(20 mL) for 12 h. After cooling to room temperature, the mixture was subjected to filtration through a celite bed and the filtrate was evaporated to dryness. The residue obtained was chromatographed on 75 g silica gel using 3:1 mixture respectively of hexanes and ethyl acetate to give the aromatic aldehyde in 90% yield; $^1$H NMR(CDCl$_3$) δ6.11(2H, s), 7.10(1H, s), 7.53 (1H, d, J=8.5), 7.67(1H, d, J=8.5), 8.65(1H, s), 10.73(1H, s); $^{13}$C NMR (CDCl$_3$)δ102.1, 102.3, 104.7, 127.4, 129.5, 129.7, 130.2, 131.2, 134.7, 148.6, 151.7, 195.6; Anal. calcd for C$_{12}$H$_7$O$_3$Br: C, 51.60; H, 2.51; found: C, 51.98; H, 2.48.

f. 2-(3,4-Methylenedioxy-6-nitophenyl)-6,7-methylenedioxy-1-naphthaldehyde

Pd(PPh$_3$)$_4$ (60 mg) and CuBr (10 mg) was added to a solution of compound 2-Bromo-6,7-methylenedioxy-1-napthaldehyde (176 mg, 0.63 mmol) and compound 3,4-methylenedioxy-6-nitrophenyl-trimethylstannane (251 mg, 0.76 mmol) in THF(20 mL). The resulted mixture was refluxed under nitrogen for 12 h. After cooling to room temperature, THF was evaporated and ethyl acetate (30 mL) was added to the residue. The resulting solution was washed with distilled water (20 mL). The two phases was seperated as much as possible and the aqueous layer was discarded. The remaining was passed through a celite bed. Seperated organic layer was washed with brine. The organic layer was dried over anhydrous sodium sulfate, filtered and evaporated in vacuo. The residue was chromatographed over 75 g of silica gel using 3:1 mixture respectively of hexanes and ethyl acetate to give the nitroaldehyde in 70% yield; $^1$H NMR (CDCl$_3$) δ6.12(2H,s), 6.21(2H, s), 6.76(1H, s), 7.09 (1H, d, J=8.4), 7.18(11H, s), 7.66(11H, s), 7.84(1H, d, J=8.4), 8.74(1H, s), 10.19(1H, s); $^{13}$C NMR(CDCl$_3$) δ102.2, 103.0, 103.8, 104.7, 105.9, 112.2, 124.4, 125.5, 127.7, 128.8, 131.4, 131.6, 133.7, 143.6, 148.6, 151.7, 156.3, 163.5, 193.3.

The intermediate stannane used in sub-part f was prepared as follows.

g. 3,4-Methylenedioxy-2-bromonitrobenzene 3,4-Methylenedioxy-bromobenzene (5 g, 23 mmol) was slowly added to a stirred solution of 35ml concentrated nitric acid and 105 ml glacial acetic acid maintained at 10° C. The reaction mixture was stirred at 15° C. for 1 h and then diluted with 200 ml ice cold water. The resulting mixture was extracted twice with 200 ml portions of ether. The combined organic phase was dried and evaporated in vacuo to give the crude product. The crude product was recrystallized from ethanol to give bright yellow needle shaped crystals of the nitro compound in 90% yield; mp 87–89° C.; IR(KBr) 1528, 1333; $^1$H NMR (CDCl$_3$) δ6.14(2H,s), 7.12(1H, s), 7.45(1H, s); $^{13}$C NMR(CDCl$_3$) δ104.0, 107.0, 109.0,114.3, 146.2, 148.0, 152.1; HRMS calcd for C$_3$H$_4$BrNO$_4$: 244.9323; found: 244.9324.

h. 3,4-Methylenedioxy-6-nitrophenyl-trimethylstannane

A mixture of hexmethylditin (3 g, 10 mmol), the compound from sub-part g (1.6 g, 6.9 mmol) and Pd(PPh$_3$)$_4$ (200 mg) in anhydrous THF (30 ml) was heated to reflux under nitrogen for 7 h. After cooling to room temperature, THF was evaporated and methylene chloride (30 ml) was added to the residue. To this mixture, potassium fluoride solution (7M, 2 ml) was added dropwise with vigorous stirring. The mixture was passed through a celite bed and the filtrate was washed with brine. The methylene chloride layer was dried over anhydrous sodium sulfate, filtered and evaporated in vacuo. The residue was chromatographed over 100 g of silica gel using 6:1 mixture respectively of hexanes and ethyl acetate to give the stannane in 60% yield; $^1$H NMR (CDCl$_3$) δ0.32(9H,s), 6.12(2H, s), 7.03(1H, s), 7.80(1H, s); $^{13}$C NMR(CDCl$_3$) δ−6.9, 103.3, 105.9, 114.7, 137.2, 147.9, 149.4, 153.4; HRMS calcd for C$_{10}$H$_{13}$NO$_4$Sn—CH$_2$: 315.9632, found: 315.9638.

Example 8

2,8,9-Tetramethoxybenzo[i]phenathridine

A mixture of 2-(3,4-dimethoxyphenyl)-6-methoxy-1-naphthaldehyde (46 mg, 0.12 mmol) in acetic acid (4 ml) and zinc dust (100 mg, 1.5 mmol) was heated to reflux for 4 h. Acetic acid was evaporated in vacuo and the residue extacted with chloroform. The chloroform solution was filtered through a celite bed. The filtrate was washed successively with saturated sodium bicarbonate solution and brine and evaporated to dryness. The residue obtained was chromatographed on 75 g silica using a 1:1 mixture of hexanes:ethyl acetate as eluent to give the title compound (27 mg, 68%): mp 207–209° C.; IR (KBr) 1620, 1487, 1215; $^1$H NMR CDCl$_3$) δ4.00 (3H, s) 4.09 (3H, s), 4.14, (3H, s), 7.33 (1H, d, J=2.6), 7.40 (1H, dd, J=9.2, 2.6), 7.62 (1H, s), 7.85 (1H,s), 8.03 (1H, d, J=9.0), 8.41 (1H, d, J=9,0), 8.77 (1H, d, J=9.2), 9.99 (1H, s); 13H NMR (CDCl$_3$) ° 55.3, 56.6, 101.9, 108.8, 110.0, 119.6, 120.8, 121.7, 124.0, 125.2, 130.4, 131.3, 133.6, 141.8, 145.9, 150.3, 151.5, 158.8; HRMS calcd for C$_{20}$H$_{17}$NO$_2$+H:320.1287; found 320.1288.

The intermediate nitro aldehyde was prepared as follows.

a. 2-(3,4-Dimethoxy-6-nitrophenyl)-6-methoxy-1-naphthaldehyde

Using a procedure similar to that described in Example 7, sub-part f, except replacing the naphthyl bromide and the stannane used therein with the requisite compounds, the nitroaldehyde was prepared; mp 158–160° C.; IR (KBr) 1677, 1518, 1328; $^1$H NMR (CDCl$_3$) δ3.92 (3H, s), 3.97 (3H, s), 4.05 (3H, s), 6.74 (1H, s), 720 (1H, d, J=2.7), 7.25 (1H, d, J=8.4), 7.35 (1H, dd, J=9.2, 2.7), 7.77 (1H, s), 7.94 (1H, d, J=8.4), 9.15 (1H, d, J=9.2), 10.20 (1H, s); $^{13}$C NMR (CDCl$_3$) δ55.8, 57.1, 107.0, 108.3, 115.0, 122., 126.4, 127.7, 127.9, 128.7, 129.4, 133.5, 135.5, 141.2, 143.0, 149.3, 153.0, 158.7, 193.6; HRMS calcd for C$_{20}$H$_{12}$NO$_6$+H:368.1134; found 367.1129.

Example 9

2,3,8-Trimethoxybenzo[i]phenanthridine

A mixture of 2-(4-methoxy-6-nitrophenyl)-6,7-dimethoxy-1-naphthaldehyde (30 mg, 0.81 mmol) in acetic acid (3 ml) and zinc dust (100 mg, 1.5 mmol) was heated to reflux for 3 hours. Acetic acid was evaporated in vacuo and the residue extacted with chloroform. The chloroform solution was filtered through a celite bed. The filtrate was washed successively with saturated sodium bicarbonate solution and brine and evaporated to dryness. The residue obtained was chromatographed on 75 g silica using a 1:1 mixture of hexanes:ethyl acetate as eluent to give the title compound (20 mg, 77%); IR (KBr) 1615, 1518, 1272; $^1$H NMR (CDCl$_3$) δ4.02 (3H, s), 4.08 (3H, s), 4.18 (3H, s), 7.33 (1H, s), 7.37 (1H, dd, J=9.1, 2.6 Hz), 7.54 (1H, d, J=2.6), 8.05 (1H, d, J=8.7), 8.42 (1H, d, J=8.7), 8.56 (1H, d, J=9.1), 10.05 (1H, s); $^{13}$C NMR δ56.1, 56.5, 56.6, 102.2, 108.6, 109.5, 119.0, 119.2, 119.3, 120.6, 124.1, 125.8, 127.6, 131.4, 131.7, 146.7, 148.4, 150.1, 151.1, 160.3; HRMS calcd for C$_{24}$H$_{12}$NO$_3$; 319.1208; found 319.1209.

The intermediate nitroaldehyde was prepared as follows.
a. 2-(4-Methoxy-6-nitrophenyl)-6,7-dimethoxy-1-naphthaldehyde (23a)

Using a procedure similar to that described in Example 7, sub-part f, except replacing the naphthyl bromide and the stannane used therein with the requsite compounds, the nitroaldehyde was prepared; mp 200–202° C.; IR (KBr) 1672, 1523, 1256; $^1$H NMR (CDCl$_3$) δ3.96 (3H, s) 4.04 (3H, s), 4.09 (3H, s), 7.14 (1H, D, J=8.1), 7.18 (1H, s), 7.20 (1H, s), 7.20 (1H, dd, J=8.3,2.6), 7.32 (1H, d, J=8.3), 7.83 (1H, d, J=2.9), 7.90 (1H, d, J=8.1), 8.87 (1H, s), 10.17 (1H, s); $^{13}$C NMR (CDCl$_3$) δ56.3, 56.6, 106.2, 107.0, 109.8, 119.4, 1125.9, 126.8, 127.5, 130.3, 133.2, 134.7, 143.9, 149.8, 150.4, 153.1, 160.4, 194.0; HRMS calcd for C$_{20}$H$_{17}$NO$_6$: 367.1056; found 367.1050.

Example 10

2,3-Dimethoxy-8,9-methylenedioxybenzo[i]phenanthridine

A mixture of 2-(3,4-methylenedioxy-6-nitrophenyl)-6,7-dimethoxy-1-naphthaldehyde (46 mg, 0.12 mmol) in acetic acid (3 mL) and zinc dust (100 mg, 1.5 mmol) was heated to reflux for 3 hours. Acetic acid was evaporated in vacuo and the residue extacted with chloroform. The chloroform solution was filtered through a celite bed. The filtrate was washed successively with saturated sodium bicarbonate solution and brine and evaporated to dryness. The residue obtained was chromatographed on 75 g silica using a 1:1 mixture of hexanes:ethyl acetate as eluent to give the title compound (32 mg, 80%); mp 171–171° C. IR (KBr) 1610, 1461, 1277; 1H NMR (CDCl$_3$), δ4.06 (3H, s), 4.15 (3H, s), 6.15 (2H, s) 7.27 (11, s). 7.54 (1H, s), 7.85(11H, s), 7.94 (1H, d, J=8.7), 8.09(1H, s), 8.15 (1H, d, J=8.7), 9.88 (1H, s); $^{13}$C NMR (CDCl$_3$) δ56.4, 56.6, 99.7, 102.3, 102.4, 107.7, 108.5, 118.5, 21.0, 121.2, 125.6, 127.7, 130.8, 131.2, 142.8, 145.9, 148.8, 149.7, 150.1; HRMS calcd for C$_{20}$H$_{15}$NO$_4$+H; 334,.1079.

The intermediate nitroaldehyde was prepared as follows.
a. 2-(3,4-Methylenedioxy-6-nitrophenyl)-6,7-dimethoxy-1-naphthaldehyde Using a procedure similar to that described in Example 7, sub-part f, except replacing the naphthyl bromide and the stannane used therein with the requsite compounds, the nitroaldehyde was prepared; mp 223–225° C.; IR (KBr) 1677, 1502, 1956; $^1$H NMR (CDCl$_3$) δ(3H, s), 4.09 (3H, s), 6.21 (2H, s), 6.78 (1H, s), 7.13 (1H, d, J=8.4), 7.18 (1H, s), 7.66 (1H, s), 7.91 (1H, d, J=8.4), 8.84 (1H, s), 10.22 (1H, s); $^{13}$C NMR (CDCl$_3$) δ56.3, 56.6, 103.9, 105.2, 107.1, 112.3, 125.4, 127.0, 127.5, 130.4, 131.6, 133.3, 143.8, 148.5, 150.1, 151.7, 153.1, 193.6,; HRMS calcd for C20H15NO7+H: 382.0927; found 382.0927

For sub-part a of Examples 8–10, the requsite intermediate naphthyl bromide can be prepared from commercially avaliable starting materials using a sequence similar to that described in Example 7, sub-parts a–d; and the requsite intermediate stannane can be prepared from commercially available starting materials using a sequence similar to thar described in Example 7, sub-parts g and h.

Example 11

The following illustrate representative pharmaceutical dosage forms, containing a compound of formula I ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula I:

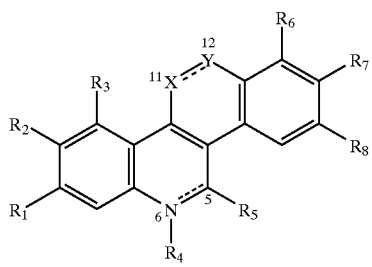

(I)

wherein
- $R_1$, $R_2$ and $R_3$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_K$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo;
- $R_4$ is oxy, $(C_1-C_6)$alkyl, or is absent;
- $R_5$ is hydrogen, hydroxy, or $(C_1-C_6)$alkyl;
- $R_6$, $R_7$ and $R_8$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_6$ and $R_7$ taken together are methylenedioxy and $R_8$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1-C_6)$alkyl, $(C_3-C_6)$cycloalkyl, $(C_1-C_6)$ alkoxy, nitro, hydroxy, $NR_gR_h$, $C(=O)R_k$, $COOR_k$, $OR_m$, or halo;
- each bond represented by ——— is individually present or absent;
- X is $C(R_a)(R_b)$ or $NR_c$;
- Y is $C(R_d)(R_e)$ or $NR_f$;
- if present, $R_a$ and $R_b$ are each independently hydrogen or $(C_1-C_6)$alkyl if the bond between the 11- and 12-positions represented by ——— is absent; or $R_a$ is hydrogen or $(C_1-C_6)$alkyl and $R_a$ is absent if the bond between the 11- and 12-positions represented by ——— is present;
- if present, $R_c$ and $R_f$ are each independently hydrogen or $(C_1-C_6)$alkyl if the bond between the 11- and 12-positions represented by ——— is absent; or $R_c$ and $R_f$ are each independently $(C_1-C_6)$alkyl or absent if the bond between the 11- and 12-positions represented by ——— is present;
- if present, $R_d$ and $R_e$ are each independently hydrogen or $(C_1-C_6)$alkyl if the bond between the 11- and 12-positions represented by ——— is absent; or $R_d$ is hydrogen or $(C_1-C_6)$alkyl and $R_e$ is absent if the bond between the 11- and 12-positions represented by ——— is present;
- each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;
- each $R_k$ is independently hydrogen, or $(C_1-C_6)$alkyl; and
- each $R_m$ is independently $(C_1-C_6)$alkanoyl, aryl, or aryl $(C_1-C_6)$alkyl;
- wherein any $(C_1-C_6)$alkyl, $(C_3-C_6)$cycloalkyl, or $(C_1-C_6)$ alkoxy of $R^1$, $R^2$, $R^3$, $R^6$, $R^7$, $R^8$, or $R_k$ is optionally substituted on carbon with 1, 2, or 3 substituents independently selected from hydroxy, halo, $NR_nR_p$, $(C_3-C_6)$cycloalkyl, or $(C_1-C_6)$alkoxy; wherein each $R_n$ and $R_p$ is independently hydrogen, $(C_1-C_6)$alkyl, $(C_3-C_6)$cycloalkyl, $(C_1-C_6)$alkoxy, or $(C_1-C_6)$ alkanoyl; or $R_n$ and $R_p$ together with the nitrogen to which they are attached are pyrrolidino, piperidino, morpholino, or thiomorpholino;
- wherein any aryl is optionally be substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, and $(C_1-C_6)$ alkoxy;
- provided that at least one of $R_2$ and $R_8$ is hydrogen, methyl, nitro, hydroxy, amino, fluoro or chloro; or at least one of $R_2$ and $R_8$ forms part of a methylenedioxy; and
- provided that $R_1-R_3$ and $R_6-R_8$ are not all hydrogen;
- provided the compound is not 9-methylbenzo[i] phenanthridine; 1-chloro-2-methoxybenzo[i] phenanthridine; 2-methoxybenzo[i]phenanthridine; 2,3-methylenedioxy-8,9-methylenedioxybenzo[i] phenanthridine; 5,8-dimethylbenzo[i]phenanthridine; 2-methoxy-5-methylbenzo[i]phenanthridine; 2-methoxy-5,8-dimethyl benzo[i]phenanthridine; 5,6-dihydro-9-methylbenzo[i]phenanthridine; or 1-chloro-2-methoxy-5,6-dihydrobenzo[i]phenanthridine;
- or a pharmaceutically acceptable salt thereof.

2. The compound of formula (I) as claimed in claim 1 wherein:
- $R_1$, $R_2$ and $R_3$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_1$ and $R_2$ taken together are methylenedioxy and $R_3$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_2$ and $R_3$ taken together are methylenedioxy and $R_1$ is hydrogen, $(C_1-C_6)$alkyl, $(C_3-C_6)$cycloalkyl, $(C_1-C_6)$ alkoxy, nitro, hydroxy, $NR_gR_h$, $COOR_k$, $OR_m$, or halo;
- $R_4$ is oxy, $(C_1-C_6)$alkyl, or is absent;
- $R_5$ is hydrogen, hydroxy, or $(C_1-C_6)$alkyl;
- $R_6$, $R_7$ and $R_8$ are each individually hydrogen, $(C_1-C_6)$ alkyl, $(C_3-C_6)$cycloalkyl, $(C_1-C_6)$alkoxy, nitro, hydroxy, $NR_gR_h$, $COOR_k$, $OR_m$, or halo; or $R_6$ and $R_7$ taken together are methylenedioxfand $R_8$ is hydrogen, $(C_1-C_6)$alkyl, $(C_3-C_6)$cycloalkyl, $(C_1-C_6)$alkoxy, nitro, hydroxy, $NR_gR_h$, $COOR_k$, $OR_m$, or halo; or $R_7$ and $R_8$ taken together are methylenedioxy and $R_6$ is hydrogen, $(C_1-C_6)$alkyl, $(C_3-C_6)$cycloalkyl, $(C_1-C_6)$ alkoxy, nitro, hydroxy, $NR_gR_h$, $COOR_k$, $OR_m$, or halo;
- each bond represented by ——— is individually present or absent;
- X is $C(R_a)(R_b)$ or $NR_c$;
- Y is $C(R_d)(R_e)$ or $NR_f$;
- if present, $R_a$ and $R_b$ are each independently hydrogen or $(C_1-C_6)$alkyl if the bond between the 11- and 12-positions represented by ——— is absent; or $R_a$ is hydrogen or $(C_1-C_6)$alkyl and $R_b$ is absent if the bond between the 11- and 12-positions represented by ——— is present;

if present, $R_c$ and $R_f$ are each independently hydrogen or $(C_1-C_6)$alkyl if the bond between the 11- and 12-positions represented by ——— is absent; or $R_c$ and $R_f$ are each independently $(C_1-C_6)$alkyl or absent if the bond between the 11- and 12-positions represented by ——— is present;

if present, $R_d$ and $R_e$ are each independently hydrogen or $(C_1-C_6)$alkyl if the bond between the 11- and 12-positions represented by ——— is absent; or $R_d$ is hydrogen or $(C_1-C_6)$alkyl and $R_e$ is absent if the bond between the 11- and 12-positions represented by ——— is present;

each $R_g$ and $R_h$ is independently hydrogen, $(C_1-C_6)$alkyl, $(C_3-C_6)$cycloalkyl, $(C_1-C_6)$alkoxy, $(C_1-C_6)$alkanoyl, aryl, aryl$(C_1-C_6)$alkyl, aryloxy, or aryl$(C_1-C_6)$alkoxy; or $R_g$ and $R_h$ together with the nitrogen to which they are attached are pyrrolidino, piperidino, morpholino, or thiomorpholino;

each $R_k$ is independently hydrogen, or $(C_1-C_6)$alkyl; and each $R_m$ is independently $(C_1-C_6)$alkanoyl, aryl, or aryl $(C_1-C_6)$alkyl;

wherein any aryl may optionally be substituted with 1, 2, or 3 substituents independently selected from hydroxy, halo, nitro, trifluoromethyl, trifluoromethoxy, carboxy, amino, $(C_1-C_6)$alkyl, $(C_3-C_6)$cycloalkyl, or $(C_1-C_6)$alkoxy;

provided that at least one of $R_2$ and $R_8$ is hydrogen, methyl, nitro, hydroxy, amino, fluoro or chloro; or at least one of $R_2$ and $R_8$ forms part of a methylenedioxy; and provided that $R_1-R_3$ and $R_6-R_8$ are not all hydrogen;

or a pharmaceutically acceptable salt thereof.

3. The compound of claim 1 wherein $R_3$ is hydrogen.

4. The compound of claim 1 wherein $R_4$ is absent and the bond between the 5- and 6-positions represented by ——— is present.

5. The compound of claim 1 wherein $R_4$ is $(C_1-C_6)$alkyl.

6. The compound of claim 1 wherein $R_5$ is methyl or hydrogen.

7. The compound of claim 1 wherein $R_1$, $R_2$ and $R_3$ are each individually hydrogen, or $(C_1-C_6)$alkoxy; or $R_1$ and $R_2$ taken together are methylenedioxy and $R_3$ is hydrogen or $(C_1-C_6)$alkoxy.

8. The compound of claim 1 wherein $R_7$ or $R_8$ is $(C_1-C_6)$ alkoxy; or $R_7$ and $R_8$ taken together are methylenedioxy.

9. The compound of claim 1 wherein $R_7$ and $R_8$ taken together are methylenedioxy.

10. The compound of claim 1 wherein $R_2$ is hydrogen, methyl, nitro, hydroxy, amino, fluoro or chloro.

11. The compound of claim 1 wherein $R_8$ is hydrogen, methyl, nitro, hydroxy, amino, fluoro or chloro.

12. The compound of claim 1 wherein the bonds represented by ——— are both present.

13. The compound of formula (I) as claimed in of claim 1 which is a compound of formula III:

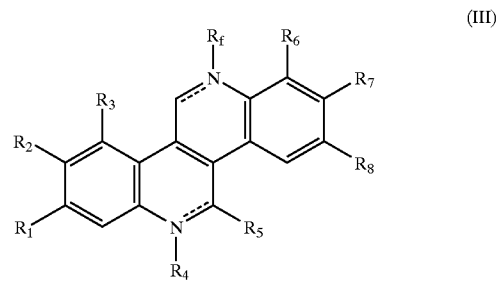

or a pharmaceutically acceptable salt thereof.

14. The compound of formula (I) as claimed in of claim 1 which is a compound of formula IV:

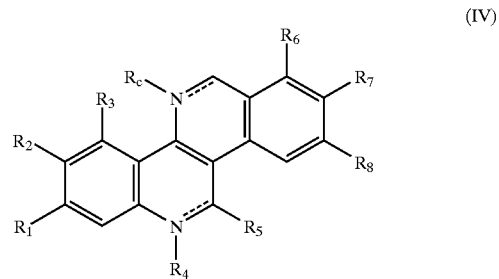

or a pharmaceutically acceptable salt thereof.

15. The compound of formula (I) as claimed in of claim 1 which is a compound of formula (V):

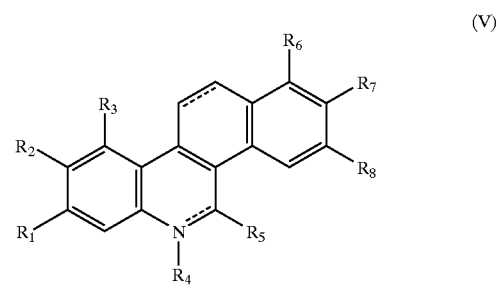

or a pharmaceutically acceptable salt thereof.

16. The compound of claim 1 wherein wherein $R_1$ is $(C_1-C_6)$alkoxy, nitro, hydroxy, or halo; or $R_1$ and $R_2$ taken together are methylenedioxy.

17. The compound of claim 1 wherein $R_2$ is $(C_1-C_6)$ alkoxy, nitro, hydroxy, or halo; or a pharmaceutically acceptable salt thereof.

18. The compound of claim 1 wherein $R_3$ is $(C_1-C_6)$ alkoxy, nitro, hydroxy, or halo; or $R_2$ and $R_3$ taken together are methylenedioxy.

19. The compound of claim 1 wherein $R_8$ is $(C_1-C_6)$ alkoxy, nitro, hydroxy or halo; or $R_7$ and $R_8$ taken together are methylenedioxy.

20. The compound of claim 1 wherein $R_7$ is $(C_1-C_6)$ alkoxy, nitro, hydroxy, or halo.

21. The compound of claim 1 wherein $R_6$ is $(C_1-C_6)$ alkoxy, nitro, hydroxy, or halo; or $R_6$ and $R_7$ taken together are methylenedioxy.

22. The compound of claim 1 which is 2,3-methylenedioxy-8,9-dimethoxybenzo[i]phenanthridine; or a pharmaceutically acceptable salt thereof.

23. A pharmaceutical composition comprising an effective amount of a compound of claim 1, in combination with a pharmaceutically acceptable diluent or carrier.

24. A method of inhibiting cancer cell growth, comprising administering to a mammal afflicted with cancer, an amount of a compound of claim 1, effective to inhibit the growth of said cancer cells.

25. A method for inhibiting cancer cell growth comprising: contacting said cancer cell in vitro or in vivo with an amount of a compound of claim 1, effective to inhibit the growth of said cancer cell.

26. The compound of claim 1 which is 2,3,8 trimethoxybenzo-[I]-phenanthridine, 2,3 dimethoxy-9-benzyloxybenzo-[I]-phenanthridine, or 2,3 dimethoxy-9-aminobenzo-[I]-phenanthridine, or pharmaceutically acceptable salts thereof.

* * * * *

UNITED STATES PATENT AND TRADEMARK OFFICE
CERTIFICATE OF CORRECTION

PATENT NO. : 6,486,167 B1   Page 1 of 1
DATED : November 26, 2002
INVENTOR(S) : Edmond J. LaVoie et al.

It is certified that error appears in the above-identified patent and that said Letters Patent is hereby corrected as shown below:

Title page,
Item [56], FOREIGN PATENT DOCUMENTS, insert -- C07D/491 -- after "5/1983".
Item [57], ABSTRACT, insert -- the -- before "specification".

Column 29,
Line 25, delete "$COOR_K$" and insert -- $COOR_k$ --, therefor.
Lines 41, 48, 51, 54, 57, 60 and 63, delete "———" and insert -- ----- -- therefor.
Line 49, delete "$R_a$" before "is absent" and insert -- $R_b$ -- therefor.

Column 30,
Line 54, delete "methylenedioxfand" and insert -- methylenedioxy and -- therefor.
Line 59, delete "$NR_gR_k$" and insert -- $NR_gR_h$ -- therefor.
Lines 61 and 67, delete "———" and insert -- ----- -- therefor.
Line 64, insert -- ) -- after "($R_d$".

Column 31,
Lines 3, 6, 10, 14, 17, 45 and 65, delete "———" and insert -- ----- -- therefor.

Signed and Sealed this

Tenth Day of February, 2004

JON W. DUDAS
*Acting Director of the United States Patent and Trademark Office*